United States Patent [19]

Schultz et al.

[11] 4,179,464

[45] Dec. 18, 1979

[54] PREPARATION OF N-(PHOSPHONOACETYL)-L-ASPARTIC ACID

[76] Inventors: Robert J. Schultz, 68 Tomcyn Dr., Amherst, N.Y. 14221; Fred W. Starks, 742 Highland Ave., Kenmore, N.Y. 14223

[21] Appl. No.: 932,501

[22] Filed: Aug. 10, 1978

Related U.S. Application Data

[63] Continuation-in-part of Ser. No. 851,382, Nov. 14, 1977, abandoned.

[51] Int. Cl.$^2$ .................................................. C07F 9/38
[52] U.S. Cl. ............................ 260/502.5; 560/171; 260/544 Y
[58] Field of Search ........................................ 260/502.5

[56] References Cited

U.S. PATENT DOCUMENTS

| | | | |
|---|---|---|---|
| 3,417,098 | 12/1968 | Anatol | 260/502.5 |
| 4,016,148 | 4/1977 | Ratcliffe et al. | 260/502.5 |

FOREIGN PATENT DOCUMENTS 1488426  6/1967  France .................................. 260/502.5

OTHER PUBLICATIONS

Vogel, "Practical Organic Chemistry" (1948), pp. 122–131.

*Primary Examiner*—Joseph E. Evans
*Attorney, Agent, or Firm*—Holman & Stern

[57] ABSTRACT

Improved methods for preparation of the tetrasodium and disodium salts of N-(phosphonoacetyl)-L-aspartic acid (PALA) are disclosed. The present methods are well suited for preparation of these products in large amounts. Particular aspects of these methods include: (1) initial preparation of the PALA moiety as the dibenzyl ester; (2) the complete removal of impurities in the form of acetic acid and sodium acetate from disodium PALA by turbulent flow precipitation; and (3) preparation and purification of the cyclohexylammonium salt of dibenzyl PALA which ultimately results in a purer final product.

7 Claims, No Drawings

PREPARATION OF N-(PHOSPHONOACETYL)-L-ASPARTIC ACID

BACKGROUND AND SUMMARY OF THE INVENTION

The invention described herein was made in the course of work under a grant or award from the Department of Health, Education and Welfare.

This is a continuation-in-part of application Ser. No. 851,382, filed Nov. 14, 1977 and now abandoned.

The present invention relates to improved methods for preparation of N-(phosphonoacetyl)-L-aspartic acid, also known as PALA, in the form of the tetrasodium or disodium salt. More particularly, the present invention is concerned with a method for the large scale preparation of the tetrasodium salt and the disodium salt of N-(phosphonoacetyl)-L-aspartic acid.

The compound, N-(phosphonoacetyl)-L-aspartic acid (PALA), was first prepared as a rationally designed transition state analogue inhibitor of aspartate transcarbamylase, as described by Stark et al., J. Biol. Chem., 246, 6599 (1971). Subsequent publications have presented an improved synthetic scheme for gram amounts of PALA, and have demonstrated inhibition of pyrimidine nucleotide biosynthesis in vitro, as discussed by Stark et al., J. Biol. Chem., 249, 6945 (1974), as well as in vivo, as discussed by Yoshida et al., J. Biol. Chem., 249, 6951 (1974). PALA has been shown to be active against the B16, Lewis Lung, and P388 tumor systems, as indicated in the NCI screening program, Selected Agents List, Drug Evaluation Branch, DR and DP, Data through Aug. 31, 1976, p. 143.

While the synthesis of PALA is straightforward, the preparation of the tetrasodium salt or the disodium salt in kilogram quantities has proven to be a major problem. The method of the present invention is particularly well suited for the production of such quantities.

DESCRIPTION OF THE PREFERRED EMBODIMENTS

One method for the preparation of the tetrasodium salt of PALA in accordance with the present invention is summarized in Reaction Scheme I. The synthesis differs from prior art procedures in various aspects, including the fact that the PALA moiety is prepared as the dibenzyl ester (IV). This dibenzyl ester is insoluble in water, thus facilitating separation from unreacted phosphonoacetyl chloride (III).

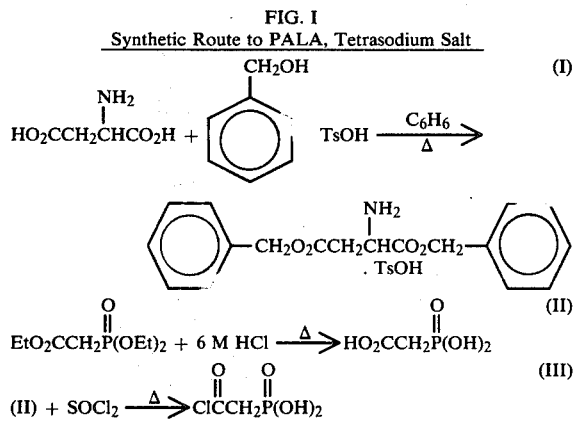

FIG. I
Synthetic Route to PALA, Tetrasodium Salt

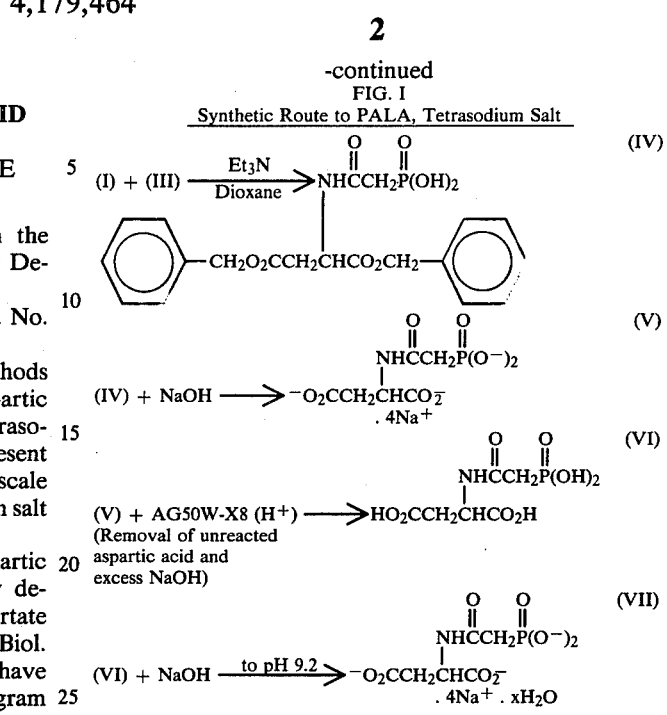

The use of the dibenzyl ester is particularly valuable for large scale production since the potentially expensive step involving chromatographic separation of PALA and phosphonoacetyl chloride is replaced by a simple water wash. A further modification of prior art procedure involves titration of PALA, free acid (VI) to pH 9.2 rather than to pH 8. This somewhat higher pH value was chosen since it corresponds to fully four moles of sodium per mole of PALA as determined from a titration curve.

Table I summarizes the batches of PALA prepared by the method of the present invention. With reference to Table I, it is pointed out that the hydrate of tetrasodium PALA contains a variable amount of water and reflects the hygroscopic nature of this tetrasodium salt. Also, differing elemental analysis results were obtained on these samples. Inconsistent comparison was obtained from both different analytical labs' tests on the same sample as well as from repeat tests by one lab on the same sample. This problem regarding elemental analyses is again believed to be due to the high degree of hygroscopicity of tetrasodium PALA.

An additional aspect with regard to the data of Table I is that the hydrogen analyses are consistently low.

Table I

| Summary of PALA . 4Na . xH$_2$O Preparation | | | | | |
|---|---|---|---|---|---|
| 1) 7.5 g. Sample | C | H | N | P | Na |
| Calc'd. for C$_6$H$_6$NO$_8$P . 4Na . 2H$_2$O | 19.01 | 2.66 | 3.69 | 8.17 | 24.26 |
| Found | 18.93 | 2.28 | 3.68 | 8.12 | 24.50 |
| 2) 48.1 q. Sample | C | H | N | P | Na |
| Calc'd. for C$_6$H$_6$NO$_8$P . 4Na . 4.9 H$_2$O . 0.15 C$_2$H$_5$OH | 17.27 | 3.84 | 3.20 | 7.07 | 20.98 |
| Found | 17.22 | 3.27 | 3.22 | 6.99 | 21.19 |
| 3) 267 q. Sample | C | H | N | P | Na |
| Calc'd. for C$_6$H$_6$NO$_8$P . 4Na . 4.5 H$_2$O | 16.99 | 3.56 | 3.30 | 7.30 | 21.68 |
| Found | 16.76 | 2.29 | 3.46 | 7.31 | 21.61 |

This discrepancy is most pronounced for item 3 of Table I, cf. 3.56% H calculated versus 2.29% found.

The reason for the low hydrogen analyses is presently not clear and is under further investigation.

An occasional problem has been the presence of excess NaOH in the tetrasodium PALA product. Tetrasodium PALA is prepared in the final step of the synthesis from the tetraacid of PALA by titration to pH 9.2 with aqueous sodium hydroxide. Conditions of the titration must be carefully controlled to prevent overtitration and concomitant excess NaOH.

In spite of the above mentioned problems involving the consistency of elemental analyses and the low hydrogen values, the tetrasodium PALA samples were characterized as highly pure materials by nmr, optical rotation (comparison with literature value), and thin layer chromatography (homogeneous in four different solvent systems). As an additional qualitative indication regarding their characterization, these samples were found to be active in the expected tumor systems.

pounds VIII and IX, on the quality of the analytical results is clear.

As indicated by Table II, tetraesters (VIII) and (IX) are readily obtained in anhydrous form and give elemental analyses with excellent agreement between the found and calculated values. For example, the maximum difference between calculated and found values of hydrogen for the tetraesters of Table II is 0.03% compared with a maximum 1.27% difference for tetrasodium PALA found in Table I.

The dibenzyl disodium PALA, (X), is markedly hygroscopic as evidenced by the degree of hydration found after pumping over $P_2O_5$. In contrast, the cyclohexylamine analogue (XI) is apparently less hygroscopic than (X) in addition to giving a better hydrogen analysis. This result suggests that an amine salt of PALA, free acid, may be significantly less hygroscopic compared to tetrasodium PALA or compared to the free acid.

Table II

Ester Derivatives of PALA

VIII.

$$\text{EtO}_2\text{CCH}_2\overset{\underset{|}{\text{NHCCH}_2\overset{O}{\overset{\|}{\text{P}}}(\text{OEt})_2}}{\underset{}{\text{CHCO}_2\text{Et}}}$$

| | C | H | N | P |
|---|---|---|---|---|
| Calc'd. for $C_{14}H_{26}NO_8P$ | 45.77 | 7.13 | 3.81 | 8.43 |
| Found | 45.88 | 7.11 | 3.81 | 8.50 |

IX.

$$\text{MeO}_2\text{CCH}_2\overset{\underset{|}{\text{NHCCH}_2\overset{O}{\overset{\|}{\text{P}}}(\text{OEt})_2}}{\underset{}{\text{CHCO}_2\text{Me}}}$$

| | C | H | N | P |
|---|---|---|---|---|
| Calc'd. for $C_{12}H_{22}NO_8P$ | 42.48 | 6.54 | 4.12 | 9.13 |
| Found | 42.50 | 6.51 | 4.09 | 9.06 |

X.

$$\text{C}_6\text{H}_5\text{—CH}_2\text{O}_2\text{CCH}_2\overset{\underset{|}{\text{NHCCH}_2\text{P}(\text{O}^-)_2 \cdot 2\text{Na}^+ \cdot 4\text{H}_2\text{O}}}{\underset{}{\text{CHCO}_2\text{CH}_2\text{—C}_6\text{H}_5}}$$

| | C | H | N | P | Na |
|---|---|---|---|---|---|
| Calc'd. for $C_{20}H_{20}NO_8P \cdot 2Na \cdot 4H_2O$ | 43.57 | 5.12 | 2.54 | 5.62 | 8.34 |
| Found | 43.95 | 4.69 | 2.50 | 5.57 | 8.31 |

XI.

$$\text{C}_6\text{H}_5\text{—CH}_2\text{O}_2\text{CCH}_2\overset{\underset{|}{\text{NHCCH}_2\text{P}(\text{OH})_2 \cdot 1.2\, C_6H_{11}NH_2 \cdot 0.8\, H_2O}}{\underset{}{\text{CHCO}_2\text{CH}_2\text{—C}_6\text{H}_5}}$$

| | C | H | N | P |
|---|---|---|---|---|
| Calc'd. for $C_{20}H_{22}NO_8P \cdot 1.2\, C_6H_{11}NH_2 \cdot 0.8\, H_2O$ | 57.43 | 6.95 | 5.42 | 5.45 |
| Found | 57.43 | 6.86 | 5.87 | 5.37 |

The difficulties associated with obtaining reproducible analyses of the hygroscopic tetrasodium PALA prompted the synthesis of various PALA esters. These less hygroscopic derivatives would be more tractable synthetically and analytically and, ideally, would have biological activity comparable to tetrasodium PALA. Table II summarizes the analytical results on these ester derivatives.

Preliminary in vivo screening results indicate that the tetraesters (VIII) and (IX) are not active and that the diesters (X) and (XI) are approximately 100 fold less active than tetrasodium PALA. Although the reduced biological activity of these PALA esters clearly rules them out as potential antineoplastic agents, the effect of drastically reduced water solubility, except for com- Favorable analytical results with alkyl esters of PALA have stimulated interest in finding nonhygroscopic PALA derivatives with retained biological activity. In this regard, developmental effort has been devoted towards the calcium salt of PALA as well as several amine salts. Retention of biological activity might be expected since these salts do not contain covalent ester bonds as in the inactive alkyl ester derivatives.

The calcium salt has been prepared by treatment of an aqueous solution of PALA, tetraacid, with calcium carbonate. The resulting calcium salt of PALA appears to have quite favorable solubility properties: it dissolves in water permitting ready formulation yet it dissolves relatively slowly thus allowing for water wash removal of soluble inorganic impurities. These results, however, should be considered tentative pending full characterization of this new calcium salt of PALA.

Preliminary studies have been directed towards isolation of solid amine salts of PALA. Cyclohexylamine, triethylenediamine, piperazine, and N,N'-dibenzylethylenediamine all appear to form solid PALA salts. In addition, the cyclohexylamine salt appears completely nonhygroscopic. Furthermore, the N,N'-dibenzylethylenediamine salt is soluble in ethanol. This latter property suggests a possible route to the sodium salt of PALA under anhydrous conditions via the amine salt in ethanolic sodium ethoxide. It should be stressed that these studies involving amine salts of PALA are preliminary. Regarding amine salts of PALA, one possible route would be the use of basic amino acids such as lysine. This would offer the advantage of using an amine with proven physiological compatability.

Further developmental work on nonhygroscopic PALA derivatives may involve study of PALA esters which could be more readily hydrolyzed than the alkyl esters (Table II) previously discussed. For example, a tetrasilyl ester of PALA would presumably be water insoluble yet quite readily hydrolyzed to PALA free acid.

As previously mentioned, the major problem in the production of PALA lies in obtaining the pure target compound, tetrasodium PALA. A chief factor is the material balance, as shown in Table III. Excluding water, the batch analyzed in Table III apparently contains 13% inorganic impurities. An apparent 15% excess of sodium indicates these contaminants to be sodium salts although further characterization is required. Since these estimates of inorganic impurities are based on material balance, the accuracy of the water assay becomes significant. Whereas the accuracy of Karl-Fisher water determination is generally in the ±5% range, the effectiveness of this method in the presence of the hygroscopic PALA should be established.

Table III

Material Balance of PALA Batch HE16-20-1

A. Direct Titrimetric Assay of Tetrasodium PALA
HCl (Aqueous): 81.4%
HClO4/HOAc (Nonaqueous): 85.6%
B. C Analysis 0.5% High
C. H2O Determination by Karl-Fisher Method: 5.7% H2O
D. Summary: Tetrasodium PALA 81.4%
Water 5.7%
87.1%
Total Impurity (Excluding Water) ~13%

NOTE: N,P,S,Cl,Si,Al are not present in impurity.

In summary, PALA batch HE16-20-1 is free of significant organic contamination (by nmr) yet contains 13% inorganic impurities. Due to the high water solubility of PALA, these inorganic impurities cannot be removed by a simple water wash so their source of introduction must be pinpointed and subsequently eliminated. The most probable identity of one of the inorganic impurities is sodium hydroxide. Recent titration data tends to exclude significant amounts of sodium hydroxide although there has been evidence of this contaminant in previous batches. It should be noted that the contaminants all could arise from conditions of high alkalinity such as those encountered during the concentration of the final product.

The most simple solution to the problem of excess alkalinity would be to formulate PALA not as the tetrasodium salt, but as the trisodium salt. The most compelling reason for this is that when formulated in water, the tetrasodium PALA will be alkaline (pH 9.2) to a degree generally considered harmful physiologically. In fact, in the original publications discussed previously concerning PALA, the tetra metal salt was not actually prepared since the PALA free acid was titrated to pH 8 rather than to pH 9.2. The intermediate salt, e.g., PALA .3.5 Li, was used preferentially to the tetralithium PALA to avoid high alkalinity in subsequent tissue studies.

The formulation of PALA at neutral pH would hopefully minimize or eliminate the problem of inorganic impurities. Should this approach fail, the development of a PALA derivative of limited water solubility would permit water-wash removal of these contaminants.

The following examples are illustrative of the preparation of the tetrasodium salt in accordance with the present invention.

EXAMPLE 1

L-Aspartic acid, dibenzyl ester p-toluenesulfonate (I)

A stirred mixture of L-aspartic acid (133 g.; 1.00 mole), benzyl alcohol (650 g.; 6.00 moles), p-toluenesulfonic acid monohydrate (194 g.; 1.02 moles), and dry benzene (400 ml.) was heated at reflux for 6.5 hours. Although benzene has been used, it is within the scope of the invention to employ other solvents such as, for example, toluene and tetrachloroethylene. The water formed in the reaction (46 ml.) was removed by means of a Dean-Stark trap. The resulting solution was cooled to room temperature then diluted with benzene (400 ml.) and ether (1200 ml.). On cooling to 10°, a white solid precipitated. This material was collected on a filter, washed with ether (1.0 l.), and dried; yield of crude (I), 384 g. (79%). A 304 g. portion of the product was recrystallized from methanol (425 ml.) to give 186 g. (61.2% recovery) of material suitable for further transformation; m.p., 155.5°–158°; literature m.p., 158°–160°.

Phosphonoacetic acid (II)

A stirred solution of triethyl phosphonoacetate (200 g.; 0.892 mole) in 6 M hydrochloric acid (1.35 l.) was heated at reflux for 6.5 hours. The solution was spin-evaporated in vacuo, then last traces of water were removed by co-evaporation with benzene (3 × 300 ml.). The oily residue crystallized on drying in vacuo over phosphorus pentoxide and potassium hydroxide. The solid material (124 g.) was recrystallized from acetic acid (270 ml.) to give 106 g. (84.4%) of product. This material was combined with 99 g. of product prepared in a similar manner and recrystallized from acetic acid (430 ml.); yield of acid (II) suitable for further transformation, 182 g. (88.9% recovery); m.p., 141°–143°; literature m.p., 143°.

Phosphonoacetyl chloride (III)

A stirred mixture of phosphonoacetic acid (II) (44.1 g.; 0.315 mole) and thionyl chloride (250 ml.) was heated at reflux for 2.5 hours. The resulting solution was concentrated in vacuo, then last traces of thionyl chloride were removed by co-evaporation with dry benzene (2 × 100 ml.). The yellow, oily residue was used in the following reaction without further characterization.

L-Aspartic acid, N-(phosphonoacetyl)-, dibenzyl ester (IV)

To a cool (15°), stirred suspension of L-aspartic acid, dibenzyl ester p-toluenesulfonate (I) (102 g.; 0.210 mole) in dry dioxane (650 ml.) was added, dropwise, triethylamine (61.1 g.; 0.604 mole) during 25 minutes. The resulting solution was stirred at 15° for 10 minutes, then phosphonoacetyl chloride (III), prepared from 0.315 mole of phosphonoacetic acid (II), dissolved in dry dioxane (400 ml.) was added, dropwise, during 1 hour. The temperature was maintained below 15° during the addition. The cooling bath was removed, and the reaction mixture was stirred for 1.5 hours. The insolubles were filtered off then washed with dioxane (50 ml.) and ether (200 ml.). The orange filtrate was concentrated in vacuo, then the oily residue was dissolved in benzene (1.5 l.). The organic solution was washed with water (5×500 ml.) and saturated sodium chloride (1×500 ml.), dried over magnesium sulfate, then evaporated in vacuo to give 80 g. (87.5%) of product. This yellow, crusty material was suitable for further transformation.

L-Aspartic acid, N-(phosphonoacetyl)-, tetrasodium salt dihydrate (PALA) (VII)

To L-aspartic acid, N-(phosphonoacetyl)-, dibenzyl ester (IV) (76.7 g.; 0.176 mole) was added a cool (10°) solution of sodium hydroxide (42.4 g.; 1.06 moles) in 1370 ml. of water. The mixture was stirred at 10°–15° for 3 hours, then the insolubles were filtered off. The filtrate was concentrated in vacuo (bath temperature <40°) to a volume of 500 ml. then extracted with methylene chloride (1×200 ml.) and ether (1×200 ml.). The aqueous solution was diluted with methanol (1.7 l.) and cooled resulting in the precipitation of an oil. After decantation, the oil was dissolved in water (100 ml.), and the solution was applied to an AG50W-X8 (hydrogen form) cation exchange resin column (5.6 cm.×13 cm.). The column was eluted with 350 ml. of water (10 fractions of 35 ml. each). Fractions 5–7, which contained the desired product as determined by TLC, were combined and evaporated in vacuo (bath temperature <30°). The oily residue was dissolved in acetone (350 ml.), charcoal (9 g.) was added, and the mixture was stirred at room temperature for 15 hours. The insolubles were filtered off, then the filtrate was evaporated in vacuo. The residue was dried to constant weight in vacuo over phosphorus pentoxide to give 17.8 g. (39.6%) of the free acid as a crusty solid. A stirred, cold (4°) solution of the tetraacid (VI) (17.8 g.; 0.070 mole) in water (200 ml.) was adjusted to pH 8 with 6.5% aqueous sodium hydroxide (140 ml.). The basic solution was spin-evaporated at reduced pressure (1–2 mm. Hg; <30°), and the residue was partially dried in vacuo over phosphorus pentoxide. The semi-solid material was triturated with acetone (4×100 ml.) and ether (1×100 ml.), then the resulting powder was collected on a filter and dried for 12 hours in vacuo at 40° over phosphorus pentoxide; yield of hydrated material containing approximately 3.5 sodiums, 18.8 g. (~68.6%). A 9.7 g. portion of the product was dissolved in 80 ml. of water. The pH of the solution was adjusted to 9.21 at 20° with 0.1 N aqueous sodium hydroxide (16 ml.). After removal of the water by lyophilization, the semi-solid was triturated with acetone (4×50 ml.). The resulting powder was dried in vacuo at room temperature over phosphorus pentoxide for 14 days to give 8.3 g. of analytically pure PALA.

The analysis of the product is shown in Table I as Sample No. 1.

Spectral Data:

Nuclear Magnetic Resonance (D$_2$O)

δ 2.57 (d, 2, J=18.6 Hz, —CH$_2$ α to P); 2.60 (3 line m, 2, —CH$_2$ α to —CH); 4.37 (d of d, 1, —CH)

| Optical Rotation: | |
|---|---|
| Observed | Literature |
| $[\alpha]_D^{25}$ + 10.30 (c, 3.798 in water) | $[\alpha]_D^{22}$ + 14.24 (c, 3.876 in water) |

The literature value is for the tetralithium salt. A more direct comparison of the optical rotations is the following molecular rotations [M]:
$[M]_D^{25}$+39.05  $[M]_D^{22}$+39.71

| Chromatography: | |
|---|---|
| Thin Layer Chromatography (Cellulose, Quanta/Gram Q2F Glass Plates) | |
| Solvent System | R$_f$ Value |
| 1. n-Butanol-acetic acid-water (5:2:3) | 0.26 |
| 2. Ethanol-water (2:3) | 0.72 |
| 3. Ethanol-ammonium hydroxide-water (6:1:3) | 0.13 |

Quantity Spotted: 40 μg.

Detection: Phospray (A commercial reagent used to visualize phosphorus containing compounds).

Results: The compound moves as one spot in each of the solvent systems. TLC of the free acid, liberated from the tetrasodium salt with hydrochloric acid, gave a negative test for aspartic acid when sprayed with ninhydrin.

EXAMPLE 2

L-Aspartic acid, dibenzyl ester p-toluenesulfonate (I)

A stirred mixture of L-aspartic acid (399 g.; 3.00 moles), benzyl alcohol (1.95 kg.; 18.0 moles), p-toluenesulfonic acid monohydrate (582 g.; 3.06 moles), and dry benzene (1.2 l.) was heated at reflux for 16 hours. The water formed in the reaction (145 ml.) was removed by means of a Dean-Stark trap. The resulting solution was cooled to room temperature, then diluted with benzene (1.2 l.) and ether (3.6 l.). The resulting solid was collected on a filter, washed with ether (7.0 l.), and dried; yield, 1195 g. (82%). The crude product was recrystallized from methanol (1720 ml.) to give 959 g. (80% recovery) of purified (I); m.p., 158°–159.5°; literature m.p., 158°–160°. Additional reactions were carried out to give a total of 4.27 kg. of product suitable for further transformation.

Phosphonoacetic acid (II)

A stirred solution of triethyl phosphonoacetate (900 g.; 4.01 moles) in 6 M hydrochloric acid (6.1 l.) was heated at reflux for 6.5 hours. The solution was concentrated in vacuo, then last traces of water were removed by co-evaporation with benzene (2×300 ml.). The solid residue was recrystallized twice from 1.0 l. of glacial acetic acid to give 342 g. (60.8%) of acid (II); m.p., 140°–141°; literature m.p., 143°. Additional reactions were carried out to give a total of 1020 g. of product suitable for further transformation.

Phosphonoacetyl chloride (III)

A stirred mixture of phosphonoacetic acid (II) (353 g.; 2.52 moles) and thionyl chloride (1730 ml.) was heated at 50°-60° for 4 hours. The resulting solution was concentrated in vacuo (aspirator pressure then 1 mm. Hg) to give 398 g. (99.6%) of product. The yellow, oily material was used in the following reaction without further characterization.

L-Aspartic acid, N-(phosphonoacetyl)-, dibenzyl ester (IV)

To a cool (15°), stirred suspension of L-aspartic acid, dibenzyl ester p-toluenesulfonate (I) (816 g.; 1.68 moles) in dry dioxane (5.2 l.) was added, dropwise, triethylamine (489 g.; 4.83 moles) during 40 minutes. The resulting solution was stirred at 15° for 30 minutes, then phosphonoacetyl chloride (III) (398 g.; 2.51 moles) dissolved in dry dioxane (600 ml.) was added, dropwise, during 1 hour. The temperature was maintained below 15° during the addition. The cooling bath was removed, and the reaction mixture was stirred for 1 hour. The insolubles were filtered off and washed with dioxane (2.4 l.). The filtrate was concentrated in vacuo, then the oil residue was dissolved in benzene (10.0 l.). The organic solution was washed with water (6×4.0 l.), dried over magnesium sulfate, then evaporated in vacuo to give 638 g. (87.2%) of product as a yellow, crusty solid. Steps (c) and (d) were repeated, on a smaller scale, to give a total of 866 g. of (IV) suitable for further transformation.

L-Aspartic acid, N-(phosphonoacetyl)-, tetrasodium salt.4.9 H₂O.0.15 C₂H₅OH (PALA) (VII)

To a cool (10°), stirred solution of sodium hydroxide (63.6 g.; 1.59 moles) in 2055 ml. of water was added, in one portion, L-aspartic acid, N-(phosphonoacetyl)-, dibenzyl ester (IV) (115 g.; 0.264 mole). The mixture was stirred at 10°-15° for 3 hours, then the insolubles were filtered off. The filtrate was concentrated in vacuo to a volume of 750 ml. then extracted with methylene chloride (1×300 ml.) and ether (1×300 ml.). The aqueous solution was diluted with ethanol (2.55 l.) and cooled, resulting in the precipitation of an oil. After decantation, the oil was dissolved in water (150 ml.), and the solution was applied to an AG50W-X8 (hydrogen form) cation exchange resin column (7.5 cm.×25 cm.). The column was eluted with 900 ml. of water (18 fractions of 50 ml. each). Fractions 10-14, which contained the desired product as determined by TLC, were combined and evaporated in vacuo (bath temperature <30°). The oil residue was dissolved in acetone (525 ml.), charcoal (13 g.) was added, and the mixture was stirred at room temperature for 18 hours. The insolubles were filtered off, then the filtrate was evaporated in vacuo. The oil residue (tetraacid; 57.1 g.) was dissolved in 500 ml. of water. The stirred solution was cooled to 10° then titrated to pH 9.2 with aqueous sodium hydroxide (725 ml. of 1 N base then 12.5 ml. of 0.1 N sodium hydroxide). The basic solution was concentrated at reduced pressure (1-2 mm. Hg; <30°) to a volume of 100 ml. then added to 2.0 l. of ethanol. The precipitated semi-solid material was triturated with ethanol (3×700 ml.), acetone (2×600 ml.), and ether (1×600 ml.). The resulting powder was collected on a filter then dried in vacuo at room temperature over phosphorus pentoxide for 5 days to give 50.8 g. (56.1%) of the desired product.

The analysis of the product is shown in Table I as Sample No. 2.

Spectral Data:

Nuclear Magnetic Resonance (D₂O)

δ 1.19 (t, 0.35, —CH₃ of EtOH); 2.49 (d, 2, J=18.0 Hz, —CH₂ α to P); 2.50 (3 line m, 2, —CH₂ α to —CH); 3.56 (q, 0.24, —CH₂ of EtOH); 4.29 (t, 1, —CH)

| Optical Rotation: | |
|---|---|
| Observed | Literature |
| $[\alpha]_D^{25}$ + 9.33 (c, 4.609 in water | $[\alpha]_D^{25}$ + 10.30 (c, 3.798 in water) |

| Chromatography: | |
|---|---|
| Thin Layer Chromatography (Cellulose, Quanta/Gram Q2F Glass Plates) | |
| Solvent System | $R_f$ Value |
| 1. n-Butanol-acetic acid-water (5:2:3) | 0.38 |
| 2. Ethanol-water (2:3) | 0.72 |
| 3. Lithium chloride (0.6 M)-ethanol-ammonium hydroxide (5:5:1) | 0.72 |

Quantity Spotted: 90 μg.
Detection: Phospray (A commercial reagent used to visualize phosphorus containing compounds).
Results: The compound moves as one spot in each of the solvent systems. TLC of the free acid, liberated from the tetrasodium salt with hydrochloric acid, gave a negative test for aspartic acid when sprayed with ninhydrin.

EXAMPLE 3

The L-aspartic acid, dibenzyl ester p-toluenesulfonate (I) and phosphonoacetic acid (II) were prepared as in Example 2.

Phosphonoacetyl chloride (III)

A stirred mixture of phosphonoacetic acid (II) (355 g.; 2.54 moles) and thionyl chloride (1770 ml.) was heated at 50°-55° for 4.5 hours. The resulting solution was concentrated in vacuo (<35°; aspirator pressure then 1 mm. Hg) to give 395.7 g. (98.3%) of product. The yellow, oily material was used in the following reaction without further characterization.

L-Aspartic acid, N-(phosphonoacetyl)-, dibenzyl ester (IV)

To a cool (15°), stirred suspension of L-aspartic acid, dibenzyl ester p-toluenesulfonate (I) (812 g.; 1.67 moles) in dry dioxane (5.2 l.) was added, dropwise, triethylamine (486 g.; 4.80 moles) during 30 minutes. The resulting solution was stirred at 15° for 30 minutes, then phosphonoacetyl chloride (III) (395.7 g.; 2.500 moles) dissolved in dry dioxane (600 ml.) was added, dropwise, during 1 hour. The temperature was maintained below 15° during the addition. The cooling bath was removed, and the reaction mixture was stirred for 1 hour. The insolubles were filtered off and washed with dioxane (2.0 l.). The filtrate was concentrated in vacuo, then the oily residue was dissolved in benzene (10.1 l.). The organic solution was washed with water (6×4.0 l.), dried over magnesium sulfate, then evaporated in vacuo to give 568 g. (78.1%) of product as a yellow, crusty solid suitable for further transformation.

L-Aspartic acid, N-(phosphonoacetyl)-, tetrasodium salt.4.5 H₂O (PALA) (VII)

To a cool (10°), stirred solution of sodium hydroxide (312 g.; 7.80 moles) in 10.0 l. of water was added, in one portion, L-aspartic acid, N-(phosphonoacetyl)-, dibenzyl ester (IV) (568 g.; 1.30 moles). The mixture was stirred at 10°-15° for 6 hours, then the insolubles were filtered off. The filtrate was concentrated in vacuo to a volume of 3.0 l. then extracted with methylene chloride (1×1.3 l.) and ether (1×1.3 l.). The aqueous solution was added to 12.0 l. of ethanol resulting in the precipitation of a semi-solid. After decantation, the material was dissolved in water (680 ml.), and equal portions of the solution were applied to two AG50W-X8 (hydrogen form) cation exchange resin columns (9.6 cm.×25 cm.). Each column was eluted with 2.0 l. of water (20 fractions of 100 ml. each). Fractions 7-14 of each column, which contained the desired product as determined by TLC, were combined and evaporated in vacuo (bath temperature <30°). The oil residue was dissolved in acetone (2.0 l.), charcoal (50 g.) was added, and the mixture was stirred at room temperature for 18 hours. The insolubles were filtered off, then the filtrate was evaporated in vacuo. The semi-solid residue (tetraacid; 227.1 g.) was dissolved in 2.0 l. of water. The stirred solution was cooled to 10° then titrated to pH 9.2 with 1 N aqueous sodium hydroxide (3123 ml.). The basic solution was concentrated at reduced pressure (1-2 mm. Hg; <30°), and the oily residue was triturated with acetone (5.8 l.). The solid material was partially dried in vacuo then triturated with acetone (2.0 l.) and ether (2.0 l.). The resulting powder was dried at reduced pressure over phosphorus pentoxide for 9 days at room temperature to give 272.2 g. of the desired product.

The analysis of the product is shown in Table I as Sample No. 3. The material balance for this batch is shown in Table III.

Spectral Data:

Nuclear Magnetic Resonance (D₂O)

δ 2.29 (m, 4, —CH₂ α to P+—CH₂ α to —CH); 4.13 (m, 1, —CH)

| Optical Rotation | |
|---|---|
| Observed | Literature |
| $[\alpha]_D^{25}$ + 9.44 (c, 3.743 in water) | $[\alpha]_D^{25}$ + 10.30 (c, 3.798 in water) |

Chromatography:

Thin Layer Chromatography
(Cellulose, Quanta/Gram Q2F Glass Plates)

| Solvent System | $R_f$ Value |
|---|---|
| 1. Ethanol-ammonium hydroxide-water (6:1:3) | 0.13 |
| 2. n-Butanol-acetic acid-water (5:2:3) | 0.30 (tailing) |
| 3. Lithium chloride (0.6 M)-ethanol-ammonium hydroxide (5:5:1) | 0.61 |
| 4. Ethanol-water (2:3) | 0.81 |

Quantity Spotted: 112 μg.

Detection: Phospray (A commercial reagent used to visualize phosphorus containing compounds).

Results: The compound moves as one spot in each of the solvent systems. TLC of the free acid, liberated from the tetrasodium salt with hydrochloric acid, gave a negative test for aspartic acid when sprayed with ninhydrin.

An additional aspect of the present invention is the preparation of the disodium salt, which may be obtained directly from the product mixture obtained on hydrolysis of dibenzyl PALA. This mixture, which includes tetrasodium PALA, disodium aspartate, and sodium hydroxide, is dissolved in glacial acetic acid. The clarified solution is then diluted with ethanol resulting in precipitation of the disodium compound.

Disodium PALA has been successfully synthesized by partial neutralization of purified tetrasodium PALA with acetic acid as described above. The desired compound has also been synthesized from the mixture obtained on hydrolysis of the N,N'-dibenzylethylenediamine salt of dibenzyl PALA (XII). This amine salt, as shown

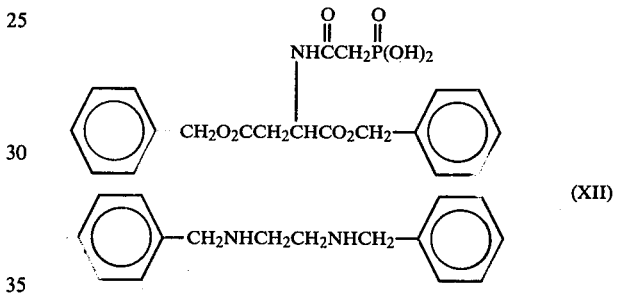

in formula (XII), gives basically the same hydrolysis mixture as dibenzyl PALA. The disodium salt obtained from (XII) is the same by chromatographic, spectral, and analytical data as that obtained from pure tetrasodium PALA.

The isolated material contains acetic acid and ethanol. These solvents can be eliminated by freezedrying. Two to three lyophilizations afford solvent free material.

The use of disodium PALA offers the following advantages: (1) a shorter time is required to synthesize the material due to (a) Complete elimination of ion exchange columns, and (b) Substantial reduction in the volume of water required to be evaporated; (2) the projected cost for 5 kg. amounts of material is at least 30% less than that for 5 kg. of tetrasodium PALA; (3) the synthesis assures a reproducible sodium content; (4) the consistently low hydrogen analyses associated with tetrasodium PALA are no longer a problem; (5) the synthesis is readily adaptable to scale-up; (6) the compound is less hygroscopic than tetrasodium PALA; and (7) the material is extremely water soluble.

The following determinations were made as to the physical properties of the disodium PALA. Except for the test for stability, these tests were carried out on material free of solvent contamination.

Hygroscopic Character. Tetrasodium PALA absorbs atmospheric moisture 1.5 times faster than the disodium salt. Both samples eventually take up enough moisture so as to lose their solid characteristics.

pH. A 2% solution of the disodium salt in water has a pH of 4.08.

Solubility. Disodium PALA has a solubility in water of >950 mg./1 ml.

Stability. A sample of disodium PALA was dried in vacuo at 140° for 15.5 hours. The nuclear magnetic resonance spectrum indicated that the material retained its structural integrity during this period. The spectrum also showed that approximately 50% of the acetic acid and ethanol was removed from the sample. Thin layer chromatography, however, showed the formation of a new, faster-running spot. This is believed to be an ester produced at the elevated temperature in the presence of ethanol and acetic acid.

EXAMPLE 4

L-Aspartic acid, dibenzyl ester p-toluenesulfonate (I)

A stirred mixture of L-aspartic acid (399 g.; 3.00 moles), benzyl alcohol (1.95 kg.; 18.0 moles), p-toluenesulfonic acid monohydrate (582 g.; 3.06 moles), and dry benzene (1.2 l.) was heated at reflux for 16.5 hours. The water formed in the reaction (155 ml.) was removed by means of a Dean-Stark trap. The resulting solution was cooled to room temperature then diluted with benzene (1.2 l.) and ether (3.6 l.). The resulting solid was collected on a filter, washed with ether (7.0 l.), and dried; yield, 1214 g. (83.3%). An additional 3868 g. (29.08 moles) of L-aspartic acid was esterified in a similar manner to give a total of 10,991 g. (70.6%) of crude (I). Recrystallization of this material from methanol (16.2 l.) afforded 7090 g. (64.5% recovery) of purified product; m.p., 154.5°–156°; literature m.p., 158°–160°. The recrystallization filtrate was spin-evaporated in vacuo to dryness. The solid residue was recrystallized from methanol (5.0 l.) to give an additional 883 g. (8.0% recovery) of material suitable for further transformation.

Phosphonoacetic acid (II)

A stirred solution of triethyl phosphonoacetate (2750 g.; 12.27 moles) in 6 M hydrocholoric acid (18.6 l.) was heated at reflux for 8 hours. The cooled solution was combined with that from an identical run and concentrated in vacuo to an oil. Last traces of water were then removed by co-evaporation with benzene (2×1.8 l.). The resulting solid was recrystallized twice from 3.6 l. of glacial acetic acid to give 1526 g. (44.4%) of acid (II); m.p., 141°–142°; literature m.p., 143°. The recrystallization filtrates were combined and spin-evaporated in vacuo to dryness. The solid material was recrystallized from glacial acetic acid (1.5 l.) to give an additional 1204 g. (35%) of product suitable for further transformation.

Phosphonoacetyl chloride (III)

A stirred mixture of phosphonoacetic acid (II) (1526 g.; 10.89 moles) and thionyl chloride (7.5 l.) was heated at 50° until a complete solution was obtained (4 hours). The dark yellow solution was evaporated in vacuo (<30°; aspirator pressure then 3–5 mm. Hg) to give 1645 g. (95.3%) of product. This orange, oily material was used in the following reaction without further characterization.

L-Aspartic acid, N-(phosphonoacetyl)-, dibenzyl ester (IV)

To a cool (15°), stirred suspension of L-aspartic acid, dibenzyl ester p-toluenesulfonate (I) (3383 g.; 6.967 moles) in dry dioxane (21.6 l.) was added, in a thin stream, triethylamine (2027 g.; 20.03 moles) during 1 hour. The resulting solution was stirred at 15° for 1.5 hours then phosphonoacetyl chloride (III) (1645 g.; 10.38 moles) dissolved in dry dioxane (4.0 l.) was added, dropwise, during 1 hour. The temperature was maintained below 15° during the addition. The cooling bath was removed, and the reaction mixture was stirred for 1 hour. The insolubles were filtered off and washed with dioxane (10.0 l.). The filtrate was concentrated in vacuo, then the oily residue was dissolved in benzene (40.0 l.). The organic solution was washed with water (4×24.0 l.), dried over magnesium sulfate, then evaporated in vacuo to give 2282 g. (75.2%) of product as a yellow, crusty solid. This material was suitable for further transformation.

L-Aspartic acid, N-(phosphonoacetyl)-, tetrasodium salt.4.5 $H_2O$ (VII)

To a cool (10°), stirred solution of sodium hydroxide (630.0 g.; 15.75 moles) in water (20.4 l.) was added L-aspartic acid, N-(phosphonoacetyl)-, dibenzyl ester (IV) (1137 g.; 2.612 moles). The mixture was stirred at 5°–15° for 6 hours, Celite (200 g.) was added, then the insolubles were filtered off. A second hydrolysis was carried out concurrently under the same conditions using 1050 g. (2.412 moles) of (IV), 580 g. (14.5 moles) of sodium hydroxide, and 18.8 l. of water. The filtrates from the two runs were combined, concentrated in vacuo (35°; 3–5 mm. Hg) to a volume of 12.0 l., then extracted with ether (3×5.0 l.). The aqueous solution was added to 45.4 l. of ethanol resulting in the precipitation of an oil. After decantation, the material was dissolved in water (2.5 l.), then AG50W-X8 (hydrogen form) cation exchange resin (9.08 kg.) was added to the aqueous solution. After stirring the mixture for 3 hours, the resin was filtered off, then the filtrate was stored overnight at 5°. Fresh resin (4.0 kg.) was added to the aqueous solution, and the mixture was stirred for 2.5 hours. The insoluble material was collected on a filter, then the filtrate was spin-evaporated at reduced pressure (30°; 3–5 mm. Hg). The oily residue was dissolved in acetone (11.9 l.), charcoal (244 g.) was added, and the mixture was stirred at room temperature for 18 hours. The insolubles were filtered off, then the filtrate was evaporated in vacuo (bath temperature, 30°). The oily residue (tetraacid; 1056 g.) was dissolved in water (8.2 l.). The stirred solution was cooled to 10° then titrated to pH 9.2 with 1 N aqueous sodium hydroxide (13.13 l.). The basic solution was concentrated at reduced pressure (30°; 3–5 mm. Hg) to an oil. This material was triturated to a semi-solid with acetone (12.0 l.) which was then partially dried in vacuo. The resulting crusty solid was ground to a powder in acetone (6.0 l.), then this material was collected on a filter and washed with ether (3×2.0 l.). The solid was dried at reduced pressure over phosphorus pentoxide for 5 days to give 857.1 g. (40.2%) of (VII).

| Anal. Calc'd. for $C_6H_6NO_8P \cdot 4$ Na $\cdot$ 4.5 $H_2O$ | | | | | |
|---|---|---|---|---|---|
| | C | H | N | P | Na |
| | 16.99 | 3.56 | 3.30 | 7.30 | 21.68 |
| Found | 16.91 | 2.67 | 3.35 | 7.28 | 21.51 |

L-Aspartic acid, N-(phosphonoacetyl)-, disodium salt.1.1 H$_2$O

L-Aspartic acid, N-(phosphonoacetyl)-, tetrasodium salt.4.5 H$_2$O(VII)(10.0 g.; 0.236 mole) was dissolved in hot (90°), glacial acetic acid (125 ml.). Celite (5 g.) was added to the hot, cloudy solution, then the insolubles were filtered off. The clear, cooled, dark yellow filtrate was diluted with ethanol (300 ml.), and the resulting mixture was stirred at room temperature for 30 minutes. The precipitated solid was collected on a filter, washed by resuspension in ethanol (3×300 ml.) and ether (1×300 ml.), then dried to give 5.7 g. (80.8%) of the disodium salt as a white powder. An additional 5.0 g. of product was prepared in a similar manner. The combined material (10.7 g.), contaminated with acetic acid and ethanol (determined by N.M.R.), was dissolved in water (250 ml.). The aqueous solution was clarified by filtration then freeze-dried. The lyophilizing process was repeated two more times, then the product was dried to constant weight in vacuo at 40° over phosphorus pentoxide; yield of analytically pure product, 9.0 g. (84.1 % recovery).

Anal.

Calc'd. for C$_6$H$_8$NO$_8$P . 2 Na . 1.1 H$_2$O

|  | C | H | N | P | Na |
|---|---|---|---|---|---|
|  | 22.60 | 3.22 | 4.39 | 9.71 | 14.42 |
| Found | 22.68 | 3.21 | 4.36 | 9.62 | 14.37 |

Spectral Data:

Nuclear Magnetic Resonance (D$_2$O)

δ 2.7 (d, 2, J=20 Hz, —CH$_2$ α to P); 2.80 (d, 2, —CH$_2$ α to —CH); 4.53 (t, 1, —CH)

Optical Rotation:

Observed $[\alpha]_D^{25}$ +15.95 (c, 2.000 in water)

Chromatography:

Thin Layer Chromatography
(Cellulose, Quanta/Gram Q2F Glass Plates)

| Solvent System | R$_f$ Value |
|---|---|
| 1. Lithium chloride (0.6 M)-ethanol-ammonium hydroxide (5:5:1) | 0.47 |
| 2. Ethanol-water (2:3) | 0.75 |
| 3. n-Butanol-acetic acid-water (5:2:3) | 0.19 |

Detection: Phospray (A commercial spray reagent used to visualize phosphorus-containing compounds).

Results: The compound moves as one spot in each of the solvent systems.

EXAMPLE 5

The L-aspartic acid, dibenzyl ester p-toluenesulfonate (I), phosphonoacetic acid (II), phosphonoacetyl chloride (III) and L-aspartic acid, N-(phosphonoacetyl)-, dibenzyl ester (IV) were prepared as in Example 2.

L-Aspartic acid, N-(phosphonoacetyl)-, tetrasodium salt, tetrahydrate (VII)

To a cool (10°), stirred solution of sodium hydroxide (289 g.; 7.23 moles) in 9.35 l. of water was added, in one portion, L-aspartic acid, N-(phosphonoacetyl)-, dibenzyl ester (IV) (523 g.; 1.20 moles). The mixture was stirred at 10°–15° for 7 hours, then the insolubles were filtered off. The filtrate was concentrated in vacuo to a volume of 3.0 l. then extracted with methylene chloride (1×1.36 l.) and ether (1×1.36 l.). The aqueous solution was added to 12.0 l. of ethanol resulting in the precipitation of a semi-solid. After decantation, the material was dissolved in water (680 ml.), and the solution was applied to an AG50W-X8 (hydrogen form) cation exchange resin column (8 cm.×46 cm.). The column was eluted with 2.7 l. of water (18 fractions of 150 ml. each). Fractions 8–16, which contained the desired product as determined by TLC, were combined and evaporated in vacuo (bath temperature <30°). The oily residue was dissolved in acetone (2.0 l.), charcoal (50 g.) was added, and the mixture was stirred at room temperature for 18 hours. The insolubles were filtered off, then the filtrate was spin-evaporated at reduced pressure. The semi-solid residue (tetraacid; 220 g.) was dissolved in water (2.0 l.). The stirred solution was cooled to 10°, then 1 N aqueous sodium hydroxide (3.29 l.) was added. The basic solution was concentrated at reduced pressure (1–2 mm. Hg; <30°), and the oily residue was triturated with acetone (5.8 l.). The semi-solid material was partially dried in vacuo then triturated to a powder with acetone (2.0 l.) and ether (2.0 l.). It was determined by elemental analysis and nuclear magnetic resonance spectroscopy that the dried powder contained excess sodium hydroxide. The solid was therefore dissolved in water (2.0 l.), and the solution was cooled to 6°. To this stirred solution (pH 13.0) was added, in portions, AG50W-X8 (hydrogen form) cation exchange resin (310 ml.) during 10 minutes. The mixture was stirred for 20 minutes, then the resin was collected on a filter and washed with water (450 ml.). The stirred filtrate (pH 6.75) was titrated to pH 9.2 with aqueous sodium hydroxide (363 ml. of 1 N base then 12 ml. of 0.1 N sodium hydroxide). After removal of the water in vacuo, the semi-solid residue was triturated with acetone (4.0 l.). The resulting powder was collected on a filter, washed with ether (3.0 l.), then dried to give 217.6 g. (43.7%) of (VII).

L-Aspartic acid, N-(phosphonoacetyl)-, disodium salt, monohydrate.0.3 acetic acid.0.1 ethanol To 2.0 l. of hot (85°), glacial acetic acid was added, in one portion, L-aspartic acid, N-(phosphonoacetyl)-, tetrasodium salt, tetrahydrate (VII)(214 g.; 0.516 mole). After stirring the mixture at 85°–90° for 30 minutes, Celite (50 g.) was added, then the insolubles were filtered off. The clear, dark yellow filtrate was cooled to room temperature and diluted with ethanol (4.5 l.). The resulting mixture was stirred for 30 minutes, then the precipitated solid was collected on a filter. The material was washed by resuspension in ethanol (2×3.5 l.) and ether (1×1.2 l.) then dried in vacuo at 55° over phosphorus pentoxide to give 111.8 g. (63.8%) of the analytically pure disodium salt.

Anal.
Cald'd. for $C_6H_8NO_8P \cdot 2\,Na \cdot H_2O \cdot 0.3\,C_2H_4O_2 \cdot 0.1\,C_2H_6O$

|  | C | H | N | P | Na |
|---|---|---|---|---|---|
|  | 24.04 | 3.50 | 4.12 | 9.12 | 13.53 |
| Found | 24.19 | 3.56 | 4.14 | 8.96 | 13.48 |

Spectral Data:

Nuclear Magnetic Resonance ($D_2O$)

$\delta$ 0.92 (t, 0.3, —$CH_3$ of ethanol); 1.83 (s, 0.9, —$CH_3$ of acetic acid); 2.55 (d, 2, J=20 Hz, —$CH_2$ α to P); 2.58 (d, 2, —$CH_2$ α to —CH); 3.33 (q, 0.2, —$CH_2$ of ethanol); 4.32 (t, 1, —CH)

Optical Rotation:

Observed $[\alpha]_D^{22}$ +15.31 (c, 2.103 in water)

Chromatography:

Thin Layer Chromatography
Quanta/Gram Q2F Glass Plates

| Solvent System | $R_f$ Value |
|---|---|
| 1. Lithium chloride (0.6 M)-ethanol-ammonium hydroxide (5:5:1) | 0.54 |
| 2. Ethanol-water (2:3) | 0.69 |
| 3. Ethanol-ammonium hydroxide-water (6:1:3) | 0.18 (elongated) |
| 4. n-Butanol-acetic acid-water (5:2:3) | 0.20 (tailing) |

Detection: Phospray (A commercial spray reagent used to visualize phosphorus-containing compounds).

Results: The compound moves as one spot in each of the solvent systems.

EXAMPLE 6

The L-aspartic acid, dibenzyl ester p-toluenesulfonate (I), phosphonoacetic acid (II), phosphonoacetyl chloride (III), L-aspartic acid, N-(phosphonoacetyl)-, dibenzyl ester (IV), and L-aspartic acid, N-(phosphonoacetyl)-, tetrasodium salt.4.5 $H_2O$ (VII) were prepared as Example 4.

L-Aspartic acid, N-(phosphonoacetyl)-, disodium salt, monohydrate.0.3 acetic acid.0.1 ethanol L-Aspartic acid, N-(phosphonoacetyl)-, tetrasodium salt.4.5 $H_2O$ (VII)(716.8 g.; 1.690 moles) was added, in one portion, to hot (95°), glacial acetic acid (7.0 l.). The mixture was stirred at 90°–95° for 45 minutes, then Celite (250 g.) was added. After stirring the hot (90°–95°) mixture for 20 minutes, the insolubles were collected on a filter and washed with acetic acid (0.5 l.). The clear, dark orange filtrate was cooled to room temperature and diluted with ethanol (16.1 l.). The resulting mixture was stirred for 1 hour, then the precipitated solid was collected on a filter. The material was suspended in ethanol (7.5 l.), and the suspension was vigorously stirred for 3 hours. The solid was collected on a filter then washed as above with ethanol (2×7.5 l.) and ether (1×7.5 l.). The material was dried in vacuo at 50°–55° over phosphorus pentoxide to give 426.5 g. (74.3%) of the analytically pure disodium salt.

Anal.
Calc'd. for $C_6H_8NO_8P \cdot 2\,Na \cdot H_2O \cdot 0.3\,C_2H_4O_2 \cdot 0.1\,C_2H_6O$

|  | C | H | N | P | Na |
|---|---|---|---|---|---|
|  | 24.04 | 3.50 | 4.12 | 9.12 | 13.53 |
| Found | 24.35 | 3.46 | 4.19 | 8.78 | 13.44 |

Spectral Data

Nuclear Magnetic Resonance ($D_2O$)

$\delta$ 0.98 (t, 0.3, —$CH_3$ of ethanol); 1.88 (s, 0.9, —$CH_3$ of acetic acid); 2.61 (d, 2, J=20 Hz, —$CH_2$ α to P); 2.63 (d, 2, —$CH_2$ α to —CH); 3.44 (q, 0.2, —$CH_2$ of ethanol); 4.36 (t, 1, —CH)

Optical Rotation

Observed $[\alpha]_D^{22}$ +14.86 (c, 1.998 in water)

Chromatography:

Thin Layer Chromatography
(Cellulose, Quanta/Gram Q2F Glass Plates)

| Solvent System | $R_f$ Value |
|---|---|
| 1. Lithium chloride (0.6 M) -ethanol-ammonium hydroxide (5:5:1) | 0.60 |
| 2. Ethanol-water (2:3) | 0.78 |
| 3. Ethanol-ammonium hydroxide-water (6:1:3) | 0.19 |
| 4. n-Butanol-acetic acid-water (5:2:3) | 0.22 (elongated) |

Quantity Spotted: 80 μg.

Detection: Phospray (A commercial spray reagent used to visualize phosphorus-containing compounds).

Results: The compound moves as one spot in each of the solvent systems.

EXAMPLE 7

L-Aspartic acid, dibenzyl ester p-toluenesulfonate (I)

A stirred mixture of L-aspartic acid (1197 g.; 9.000 moles), benzyl alcohol (5850 g.; 54.00 moles), p-toluenesulfonic acid monohydrate (1746 g.; 9.180 moles), and benzene (3.6 l.) was heated at reflux for 12 hours. The water formed in the reaction (480 ml.) was removed by means of a Dean-Stark trap. The reaction solution was cooled to room temperature then diluted with benzene (3.6 l.) and ether (10.8 l.). The resulting solid was collected on a filter, washed with ether (12.0 l.), and air dried; yield, 3646 g. (83.4%). Recrystallization of this material from methanol (6.0 l.) afforded purified (I); m.p., 158.5°–160.5°; literature m.p., 158°–160°. Four additional esterifications and recrystallizations were carried out on the same scale. The material from the five runs was combined to give 10,310 g. (57.6% recovery) of product suitable for further transformation.

Phosphonoacetic acid (II)

A stirred solution of triethyl phosphonoacetate (2200 g.; 9.813 moles) in 6 M hydrochloric acid (14.9 l.) was heated at reflux for 13 hours. The cooled solution was combined with that from an identical run and concentrated in vacuo to an oil. Last traces of water were removed by co-evaporation with benzene (2×1.2 l.), then the resulting solid was recrystallized twice from glacial acetic acid (2.2 l. then 3.3 l.). The collected material was washed with ether (4.0 l.) then dried to constant weight by spin-evaporation in vacuo (35°; 3–5 mm. Hg); yield of acid (II), 1767 g. (64.3%); m.p., 142°–143°; literature m.p., 143°. Additional reactions were performed to give a total of 3501 g. of product suitable for further transformation.

Phosphonoacetyl chloride (III)

A stirred mixture of phosphonoacetic acid (II) (1500 g.; 10.71 moles) and thionyl chloride (7.5 l.) was heated at 50° until a complete solution was obtained (5 hours). The dark yellow solution was evaporated in vacuo (<30°; aspirator pressure then 3–5 mm Hg) to give 1565 g. (92.2%) of product. This orange, oily material was used in the following reaction without further characterization.

L-Aspartic acid, N-(phosphonoacetyl)-, dibenzyl ester(IV)

To a stirred suspension of L-aspartic acid, dibenzyl ester p-toluenesulfonate (I) (3000 g.; 6.178 moles) in dry dioxane (21.6 l.) was added, in a thin stream, triethylamine (2800 g.; 27.67 moles) during 0.5 hour. The resulting solution was cooled to 15°, then phosphonoacetyl chloride (III) (1565 g.; 9.875 moles) dissolved in dry dioxane (4.4 l.) was added, dropwise, during 2 hours. The temperature was maintained below 15° during the addition. The cooling bath was removed, and the reaction mixture was stirred for 1.5 hours. The insolubles were filtered off and washed with dioxane (3×4.0 l.). The filtrate was concentrated in vacuo, then the oily residue was dissolved in methylene chloride (25.0 l.). The organic solution was washed with water (6×16.0 l.) and saturated sodium chloride solution (1×10.0 l.), dried over sodium sulfate, then evaporated in vacuo to a viscous oil; yield of (IV), 2475 g. (92.0%). Preparation of III and IV were repeated, on the same scale, to give an additional 2449 g. (91.0%) of product suitable for further transformation.

L-Aspartic acid, N-(phosphonoacetyl)-, dibenzyl ester, compd. with N,N'-dibenzylethylenediamine (XII)

To a cool (5°), stirred solution of L-aspartic acid, N-(phosphonoacetyl)-, dibenzyl ester (IV)(2449 g.; 5.625 moles) in methylene chloride (9.5 l.) was added, dropwise, N,N'-dibenzylethylenediamine (1488 g.; 6.191 moles) dissolved in methylene chloride (1.65 l.) during 3.0 hours. The temperature was maintained below 15° during the addition. After removing the cooling bath, the reaction solution was stirred at room temperature for 16 hours then concentrated in vacuo to an oil. The residue was dissolved in acetone (5.0 l.), and the solution was stored overnight (18 hours) at room temperature. A finely divided, white solid, which had precipitated from solution, was filtered off, then the filtrate was evaporated at reduced pressure. The crude material was dissolved in ethyl acetate (12.0 l.). The organic solution was washed with water (3×3.5 l.), dried over magnesium sulfate, stirred with Norit A (125 g.) for 45 minutes, then spin-evaporated in vacuo. The residue ("glass") was triturated to a powder by vigorous stirring with ether-petroleum ether (b.p., 30°–60°) (5.0 l.: 7.0 l.). The solid product was collected on a filter then dried to give 1609 g. of the tan colored salt; m.p., >300°. An additional reaction was carried out in a similar manner to give a total of 2308.5 g. of (XII) suitable for the further transformation.

L-Aspartic acid, N-(phosphonoacetyl)-, tetrasodium salt (V)

To a cool (14°), stirred solution of sodium hydroxide (240 g.; 6.00 moles) in water (7.8 l.) was added, in portions, thoroughly pulverized L-aspartic acid, N-(phosphonoacetyl)-,dibenzyl ester, compd. with N,N'-dibenzylethylenediamine (XII) (675.7 g.; 1.00 mole if (XII) is a mono salt) during 5 minutes. The reaction mixture was stirred at 10°–15° for 6 hours, Celite (250 g.) was added, then the insolubles were filtered off. The filtrate was extracted with methylene chloride (2×1.5 l.) and ether (1×1.5 l.) then concentrated in vacuo (<40°; 3–5 mm Hg). The aqueous solution (3.8 l. volume) was clarified by filtration and diluted with ethanol (13.5 l.) resulting in the precipitation of an oil. After standing for 18 hours at room temperature, the aqueous ethanol solution was removed leaving 600 ml. of crude (V) as an orange oil. Additional hydrolyses were carried out in a similar manner to give a total of 1350 ml. of oil suitable for further transformation.

L-Aspartic acid, N-(phosphonoacetyl)-, disodium salt.0.2 H₂O.0.2 sodium acetate.0.4 acetic acid.0.15 ethanol L-Aspartic acid, N-(phosphonoacetyl)-, tetrasodium salt (V) (1350 ml. of oil) was dissolved in glacial acetic acid (6.5 l.) at room temperature. The orange solution was stirred for 30 minutes, clarified by filtration, then diluted with ethanol (18.0 l.). The resulting mixture was stirred for 1 hour, then the solvent was removed using filter candles. The solid was suspended in ethanol (10.5 l.) and the mixture was vigorously stirred for 1 hour. The ethanol was drawn off as above, then the material was washed twice more with ethanol (10.5 l. then 6.0 l.). The solid was collected on three filters, under a nitrogen atmosphere, washed with ether (2×1.0 l./funnel), then partially dried by spin-evaporation at reduced pressure (30°–45°; aspirator then 3–5 mm Hg). The lumpy solid was thoroughly pulverized, under nitrogen, then dried in vacuo over phosphorus pentoxide (33.5 hours at room temperature and 12.5 hours at 50°) to give 945.1 g. of the analytically pure desired product.

Anal.

Calc'd. for $C_6H_8NO_8P \cdot 2\ Na \cdot 0.2\ H_2O \cdot 0.2\ C_2H_3O_2Na \cdot 0.4\ C_2H_4O_2 \cdot 0.15\ C_2H_6O$

|  | C | H | N | P | Na |
|---|---|---|---|---|---|
|  | 25.74 | 3.31 | 4.00 | 8.85 | 14.45 |
| Found | 25.55 | 3.35 | 4.06 | 9.19 | 14.30 |

Spectral Data

Nuclear Magnetic Resonance (D₂O)

δ 0.89 (t, 0.45, —CH₃ of ethanol); 1.78 (s, 1.8, —CH₃ of acetate+acetic acid); 2.54 (d, 2, —CH₂ α to —CH); 2.54 (d, 2, J=20.3 Hz, —CH₂ α to P); 3.36 (q, 0.30, —CH₂ of ethanol); 4.28 (t, 1, —CH).

| Optical Rotation: | |
|---|---|
| Observed | Literature |
| $[\alpha]_D^{22} + 16.39$ (c, 1.885 in water) | $[\alpha]_D^{22} + 14.86$ (c, 1.998 in water) |

| Chromatography | |
|---|---|
| Thin Layer Chromatography (Cellulose, Quanta/Gram Q2F Glass Plates) | |
| Solvent System | R_f Value |
| 1. Lithium chloride (0.6 M)-ethanol-ammonium hydroxide (5:5:1) | 0.64 |
| 2. Ethanol-water (2:3) | 0.78 |
| 3. Ethanol-ammonium hydroxide-water (6:1:3) | (elongated) 0.24 |
| 4. n-Butanol-acetic acid-water (5:2:3) | (tailing) 0.28 |

Detection: Phospray (A commercial spray reagent used to visualize phosphorus-containing compounds).

Results: The compound moves as one spot in each of the solvent systems.

EXAMPLE 8

L-Aspartic acid, dibenzyl ester p-toluenesulfonate (I)

A stirred mixture of L-aspartic acid (1197 g.; 9.000 moles) benzyl alcohol (5850 g.; 54.00 moles), p-toluenesulfonic acid monohydrate (1746 g.; 9.180 moles), and benzene (3.6 l.) was heated at reflux for 12 hours. The water formed in the reaction (480 ml.) was removed by means of a Dean-Stark trap. The reaction solution was cooled to room temperature then diluted with benzene (3.6 l.) and ether (10.8 l.). The resulting solid was collected on a filter, washed with ether (12.0 l.), and air dried; yield, 3646 g. (83.4%). Recrystallization of that material from methanol (6.0 l.) afforded purified (I); m.p., 158.5°–160.5°; literature m.p., 158°–160°. Four additional esterifications and recrystallizations were carried out on the same scale. The material from the five runs was blended together to give 10,310 g. (57.6% recovery) of (I). Additional reactions were carried out in a similar manner to give a total of 20,625 g. of product suitable for further transformation.

PHOSPHONOACETIC ACID (II)

A stirred solution of triethyl phosphonoacetate (2200 g.; 9.813 moles) in 6 M hydrochloric acid (14.9 l.) was heated at reflux for 13 hours. The cooled solution was combined with that from an identical run and concentrated in vacuo to an oil. Last traces of water were removed by co-evaporation with benzene (2×1.2 l.), then the resulting solid was recrystallized twice from glacial acetic acid (2.2 l. then 3.3 l.). The collected material was washed with ether (4.0 l.) then dried to constant weight by spin-evaporation in vacuo (35°; 3–5 mm. Hg); yield of acid (II), 1767 g. (64.3%); m.p., 142°–143°; literature m.p., 143°. Additional reactions were performed to give a total of 7994 g. of product suitable for further transformation.

PHOSPHONOACETYL CHLORIDE (III)

A stirred mixture of phosphonoacetic acid (II) (2151 g.; 15.36 moles) and thionyl chloride (10.5 l.) was heated at 50°–55° until a complete solution was obtained (5 hours). The dark yellow solution was evaporated in vacuo (<40°; aspirator pressure then 3–5 mm. Hg) to give 2236 g. (91.9%) of product. This red, viscous oil was used in the following reaction without further characterization.

L-Aspartic acid, N-(phosphonoacetyl)-, dibenzyl ester (IV)

To a cool (10°), stirred suspension of L-aspartic acid, diabenzyl ester p-toluenesulfonate (I) (5785 g.; 11.91 moles) in dry dioxane (30.0 l.) was added, in one portion, triethylamine (3238 g.; 32.00 moles). The resulting solution was stirred for 1 hour then phosphonoacetyl chloride (III) (2236 g.; 14.11 moles) dissolved in dry dioxane (5.5 l.) was added, dropwise, during 3 hours. The temperature was maintained below 30° during the addition. The cooling bath was removed, and the reaction mixture was stirred for 1 hour. The insolubles were filtered off and washed with dioxane (12.0 l.). The filtrate was concentrated in vacuo, then the oily residue was dissolved in methylene chloride (64.0 l.). The organic solution was washed with water (6×19.0 l.), dried over sodium sulfate, then evaporated at reduced pressure to a volume of 5.0 l. An 84 ml. aliquot of the solution was evaporated to dryness. The dark yellow, crusty residue was then dried to a constant weight of 84.0 g.; reaction yield, 5000 g. (96.4%). Preparation of III and IV were repeated in a similar manner to give a total of 14,941 g. of product suitable for further transformation.

L-Aspartic acid, N-(phosphonoacetyl)-, tetrasodium salt (V)

To a cool (15°), stirred solution of sodium hydroxide (1323 g.; 33.08 moles) in water (43.0 l.) was added, in one portion, 2.4 l. of the above prepared methylene chloride solution of L-aspartic acid, N-(phosphonoacetyl)-, dibenzyl ester (IV) (2.4 l.=2400 g.; 5.512 moles). The reaction mixture was stirred at 10°–15° for 8 hours, Celite (825 g.) was added, then the insolubles were filtered off (600 g. Celite pad). The filtrate was extracted with methylene chloride (2×9.0 l.) and ether (1×9.0 l.). The aqueous solution was combined with that from an identical run and concentrated in vacuo (<35°; 3–5 mm. Hg). The solution (25.0 l. volume) was clarified by filtration (400 g. Celite pad) and diluted with ethanol (88.0 l.) resulting in the precipitation of an oil. After standing for 7.5 hours at room temperature, the aqueous ethanol solution was removed leaving 4.4 l. of crude (V) as an orange oil. An additional 6695 g. of (IV) was hydrolyzed in a similar manner to give a total of 9.98 l. of oil suitable for further transformation.

L-Aspartic acid, N-(phosphonoacetyl)-, disodium salt

L-Aspartic acid, N-(phosphonoacetyl)-, tetrasodium salt (V) (4.4 l. of oil) was dissolved in glacial acetic acid (14.0 l.) at room temperature. The orange solution was stirred for 1 hour, clarified by filtration, then diluted with ethanol (44.0 l.). The resulting mixture was stirred for 1.5 hours, then the solvent was removed using filter candles. The solid was suspended in ethanol (30.0 l.), and the mixture was vigorously stirred for 2 hours. The ethanol was drawn off as above, then the material was washed by resuspension in ethanol (2×33.0 l.) and ether (1×14.0 l.). The solid was collected on two filters, under a nitrogen atmosphere, then partially dried by spin-evaporation in vacuo (30°–45°; aspirator pressure then 3–5 mm Hg). An additional 2.93 l. of oil (V) was reacted in a similar manner. The combined lumpy material was thoroughly pulverized, under nitrogen, then dried in vacuo over phosphorus pentoxide (40 hours at room temperature and 17 hours at 45°–50°) to give 4562.5 g. of a light yellow powder. The nuclear magnetic resonance spectrum and elemental analysis of this material revealed the presence of sodium acetate (0.1 mole), acetic acid (0.5 mole), and ethanol (0.15 mole). A 2000 g. portion of the product was added, in portions, to 11.5 l. of vigorously stirred glacial acetic acid during 20 minutes. The mixture was stirred at room temperature for 1 hour, then the solution was clarified by filtration. The filtrate was diluted with ethanol (26.0 l.), and the resulting mixture was stirred for 2 hours. The solvent was removed (filter candles), then the solid was washed twice by resuspension in ethanol (7.0 l. then 15.0 l.), collected on a filter, and dried by spin-evaporation at reduced pressure. The white solid (1989 g.) was determined by nuclear magnetic resonance to contain acetic acid (1.25 moles) and ethanol (0.24 mole). A 1974 g. quantity of the material was dissolved in water (4.0 l.), and the aqueous solution was diluted with ethanol (16.0 l.). The resulting mixture was stirred for 30 minutes, then the precipitated oil was allowed to settle. The aqueous ethanol solution was removed, and the oil was washed once with ethanol (3.5 l.). This material, which contained acetic acid (0.03 mole) and ethanol (0.8 mole) as determined by nuclear magnetic resonance, was dissolved in water (32.0 l.). The aqueous solution was clarified by filtration then freeze-dried to give 1512.4 g. of a flocculant, yellow solid.

Anal.
Calc'd. for $C_6H_8NO_8P \cdot 2\,Na \cdot H_2O \cdot 0.03\,C_2H_4O_2 \cdot 0.35\,C_2H_6O$

|  | C | H | N | P | Na |
|---|---|---|---|---|---|
|  | 24.23 | 3.68 | 4.18 | 9.24 | 13.72 |
| Found | 24.39 | 3.56 | 4.15 | 9.03 | 13.44 |

Spectral Data:

Nuclear Magnetic Resonance ($D_2O$)

$\delta$ 1.19 (t, —$CH_3$ of ethanol); 2.11 (s, —$CH_3$ of acetic acid); 2.83 (d, 2, J=20 Hz, —$CH_2$ $\alpha$ to P); 2.87 (d, 2, —$CH_2$ $\alpha$ to —CH); 3.67 (q, —$CH_2$ of ethanol); 4.61 (t, 1, —CH)

| Optical Rotation: | |
|---|---|
| Observed | Literature |
| $[\alpha]_D^{22}$ + 14.68 (c, 1.873 in water) | $[\alpha]_D^{22}$ + 14.86 (c, 1.998 in water) |

Chromatography

| Thin Layer Chromatography (Cellulose, Quanta/Gram Q2F Glass Plates) | |
|---|---|
| Solvent System | $R_f$ Value |
| 1. Lithium chloride (0.6 M)-ethanol-ammonium hydroxide (5:5:1) | 0.66 |
| 2. Ethanol-water (2:3) | 0.83 |
| 3. Ethanol-ammonium hydroxide-water (6:1:3) | (elongated) 0.31 |
| 4. n-Butanol-acetic acid-water (5:2:3) | 0.28 |

Detection: Phospray (A commercial spray reagent used to visualize phosphorus-containing compounds).

Results: The compound moves as one spot in each of the solvent systems.

A method for the preparation of the disodium salt of PALA in accordance with the present invention is summarized in Reaction Scheme II. As can be seen in FIG. II, the present method includes the initial preparation of phosphonoacetyl chloride. Phosphonoacetyl chloride was originally prepared in thionyl chloride at 60° C. The excess thionyl chloride was removed by evaporation in vacuo, then the oily residue was dissolved in dioxane. This solution was then added to dibenzyl aspartate in dioxane containing triethylamine at ~15°. The insoluble triethylamine hydrochloride was filtered off, the dioxane was removed at reduced pressure, then the residue was dissolved in benzene. This was later changed to methylene chloride because of the OSHA restrictions on the use of benzene.

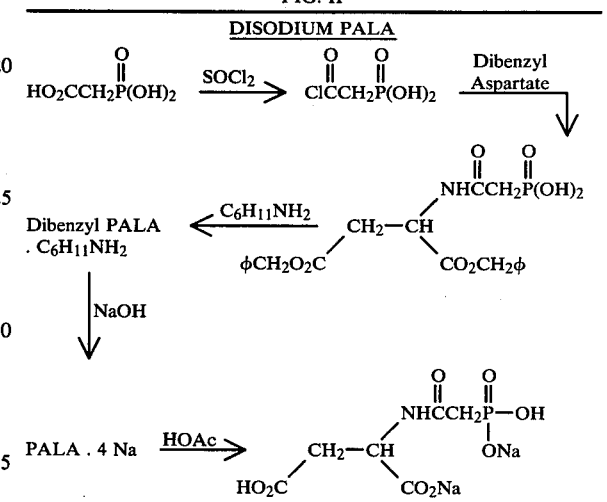

FIG. II

The organic solution was then washed several times with water in order to remove unreacted acid chloride.

This procedure was acceptable on a small scale, however, many changes were necessary in order to have a suitable production process.

Removal of the excess thionyl chloride in the preparation of phosphonoacetyl chloride posed a major problem for scale-up. The reaction was therefore attempted with one equivalent of thionyl chloride in dioxane. It was observed that, under completely anhydrous conditions, the reaction with dibenzyl aspartate gave ~70-80% of an unknown material. With the assumption that over chlorination was occurring, it seemed likely that, under the appropriate conditions, the P-Cl bond could be hydrolyzed by the addition of water. This proved to be the case. The chlorination has been successfully carried out in dioxane using from about 2.0 to 2.1 equivalents of thionyl chloride followed by the addition of from about 1.0 to 1.2 equivalents of water. The dibenzyl PALA obtained in this manner still contains a small amount of the unknown impurity. However, this can be eliminated through a salt formation or through formation of the cyclohexylammonium salt.

Other necessary modifications were made in order to improve the scale-up capability of the process. Dioxane, because of its flammable and toxic properties, was unattractive for large scale runs. A suitable substitute for the chlorination reaction proved to be a mixture of glyme (1,2-dimethoxyethane) and methylene chloride in a volume ratio of 40:60. This solvent mixture is less toxic than dioxane and was determined to be nonflammable.

In an effort to overcome the purity problem associated with tetrasodium PALA, an attempt was made to purify the salt by recrystallization. Glacial acetic acid was the first solvent chosen for this purpose, with the method being carried out as shown in Reaction Scheme III.

Tetrasodium PALA dissolved in warm, glacial acetic acid but remained in solution on cooling. On the addition of ethanol, however, a white solid was precipitated.

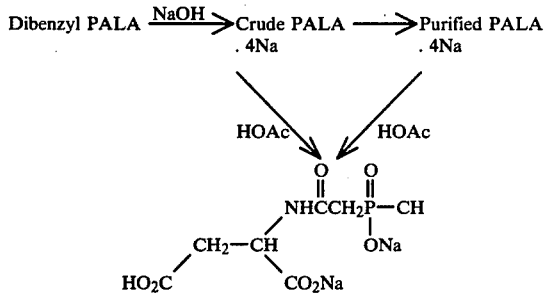

FIG. III
DISODIUM PALA

Elemental analysis of this material showed it to be the disodium salt.

Disodium PALA offers certain advantages over the tetrasodium compound, including the following:

(1) It is obtained directly in a solid form which eliminates the difficult and time consuming trituration procedure necessary to solidify the tetrasodium salt;
(2) It is less hygroscopic than the tetrasodium compound;
(3) It was determined that the compound could be prepared directly from the product mixture obtained on hydrolysis of the dibenzyl PALA. This resulted in a shorter synthesis time and reduction in production costs. This also eliminated the ion exchange process shown in Reaction Scheme I.
(4) The problem of over/or under titration associated with the preparation of tetrasodium PALA was eliminated;
(5) Consistently low hydrogen analyses were obtained for the tetrasodium salt which was no longer a problem with the disodium compound;
(6) The synthesis was more adaptable to scale-up; and
(7) A good material balance was obtained for the disodium compound. This indicated that the unknown inorganic impurities were eliminated from the isolated product.

The general procedure for the preparation of disodium PALA is shown in Reaction Scheme IV.

Dibenzyl PALA was prepared from phosphonoacetyl chloride and dibenzyl aspartate, then hydrolyzed with dilute, aqueous sodium hydroxide. The crude tetrasodium salt was then converted to disodium PALA by partial neutralization with glacial acetic acid. This basic scheme was used to synthesize 25 kg. of the target compound and is currently being used for the production of 60 kg. of the disodium salt.

In order to prepare 60 kilograms of disodium PALA, about 250 kilos of dibenzyl aspartate must be made to obtain the target quantity. The following is an illustration of the steps employed and their application in going from a simple, classical esterification reaction to multikilogram production.

Reaction Scheme V shows the esterification of aspartic acid.

This type of reaction is normally carried out in toluene or benzene with an acid catalyst. The equilibrium is shifted to give the ester by distilling off the water azeotrope. The organic solvent is returned to the reaction flask. This is the way the ester is formed for small scale work. However, to produce more than 500 pounds fast enough to service the needs of the present invention, major alterations must be made.

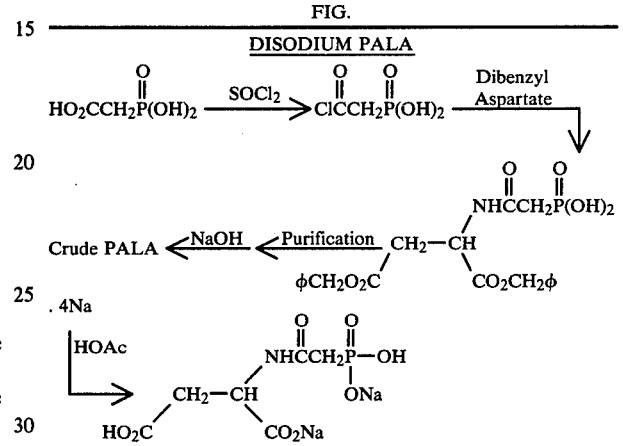

FIG.
DISODIUM PALA

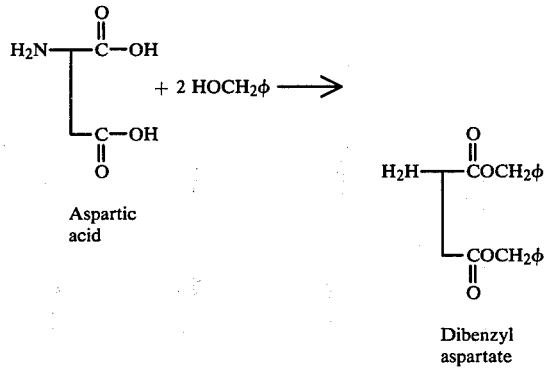

FIG. V

Aspartic acid

Dibenzyl aspartate

In preparing dibenzyl aspartate, perchloroethylene was the solvent of choice. Its lack of flammability shortened the development time, appreciably, because of the ease in handling. This solvent forms an excellent azeotrope with water. It boils high enough that the large-scale esterification is soon completed (within 3 hours) and, at the same time, the product stability is not affected by the temperature—at least during this short time of thermal contact.

A stoichiometric amount of p-toluenesulfonic acid was found to be most advantageous, and the optimum amount of benzyl alcohol was found to be 4.5 moles per mole of aspartic acid. However, laboratory runs demonstrated that when these components and the solvent were charged to the reactor at room temperature, the mass would solidify. The problem was solved by heating the solution of perchloroethylene, aspartic acid and benzyl alcohol to 65°–75° C. Then the p-toluenesulfonic acid was added. No insoluble salt formation occurred.

In a similar fashion, after esterification was completed, the reactor must be discharged at 80°–90° C.

Process control methods were devised based on thin layer chromatographic examination of the reaction mixture. The optimum time for esterification was determined by TLC. Moreover, TLC markers of possible side-products were obtained to relieve concern as to any tangential reactions. For example, the possible reaction of the toluenesulfonic acid with the amine of aspartic acid leading to the sulfonamide was shown not to occur under the conditions of the desired esterification.

By retaining the product as the tosylate salt, the reactor could be discharged directly into an optimum volume of acetone. The acetone was cooled with dry-ice. The pure ester precipitated immediately and only needed to be washed with acetone before being dried. The product was of sufficient quality that no impurities were carried into subsequent steps in the production of PALA. Dibenzyl aspartate quality control included the established characteristics in IR, NMR, optical rotation, and elemental analyses.

The development of the present process is illustrated by the results of development runs which are summarized in Table IV.

Table IV

| Reactor Size | Amount Aspartic Acid | Yield (%) | Amount of Ester |
|---|---|---|---|
| 250 ml. | 13 g. | 60–75 | — |
| 3 liter | 133 g. | 65–75 | — |
| 76 liter (20 gallon) | 3,200 g. | 64 | 7,400 g. |
| 76 liter (20 gallon) | 3,200 g. | 72 | 8,400 g. |
| 380 liter (100 gallon) | 16,000 g. | 64 | 37,500 g. |
| 380 liter (100 gallon) | 16,000 g. | 68 | 39,000 g. |

Good yield retention has been obtained on scale-up. The purity is equal to or greater than 99% from the process with a present yield of about 65%. The production per unit time is only limited by the size of the reactor. Moveover, the process information is developed to a level for easy transfer to larger equipment.

The preparation of disodium PALA, as outlined in Reaction Scheme IV, results in a product contaminated with sodium aspartate, sodium acetate, unknown phosphorus-containing materials and the solvents acetic acid and ethanol.

The dibenzyl PALA used for hydrolysis contains unreacted dibenzyl aspartate which leads to sodium aspartate under the reaction conditions. The sodium acetate arises from the partial neutralization of the tetrasodium PALA and from the excess sodium hydroxide used in the hydrolysis.

Two impurities which require elimination are acetic acid and sodium acetate. On a 500 g. scale, all of the sodium acetate and most of the acetic acid can be removed by extensive washing with ethanol. On a larger scale, this did not prove to be the case. The sodium acetate could be removed, however, by a second precipitation from acetic acid.

On a 10 g. run, the ethanol and acetic acid were completely eliminated by freeze-drying; however, this method was not operable when scaled up to 2 kg. This is an example of one of the vagaries of scale-up technology. This problem was solved by precipitating the crude disodium PALA twice from water using ethanol. This method removed all of the acetic acid and sodium acetate. The second precipitation is a dropwise addition of an aqueous solution of PALA to the vortex of vigorously stirred ethanol. The disodium salt precipitates as a granular solid. This method is suitable for quantities up to about 2 kg. For 25 kg. of the target material, this step alone would require almost 400 gallons of ethanol; for 60 kg., nearly 1000 gallons of ethanol would be needed.

It has now been determined that washing the PALA which is precipitated from the acetic acid with an appropriate water-ethanol solution completely removes the acetic acid and sodium acetate. This practical leaching procedure reduces the volume of ethanol by at least 50% and results in the saving of considerable manhours. An additional problem of ethanol solvation had existed. EtOH concentration in the end product was at a 6–9% level. The leaching process causes a substitution of solvates, i.e. water for ethanol, thus reducing the ethanol to an acceptable 1 to 2%.

Thus there is provided a process that reduces acetic acid, sodium acetate, and ethanol impurities to acceptable levels. Two major contaminants must still be controlled. These are aspartic acid and the unidentified phosphorus compounds.

The aspartic acid can be detected on TLC by spraying with ninhydrin. PALA is visualized on the chromatogram using a molybdate spray and appears as one spot in all of the solvent systems employed. However, a number of phosphorus impurities, totaling 6% could be detected using $P^{31}$ NMR. It was believed that these phosphorus impurities did not originate during either the hydrolysis or neutralization steps. As they were not present in the starting phosphonoacetic acid, they had to be formed during the preparation of the dibenzyl PALA. This was confirmed by $P^{31}$NMR which contained peaks other than that attributed to dibenzyl PALA.

FIG. VI

PURIFICATION OF DIBENZYL PALA

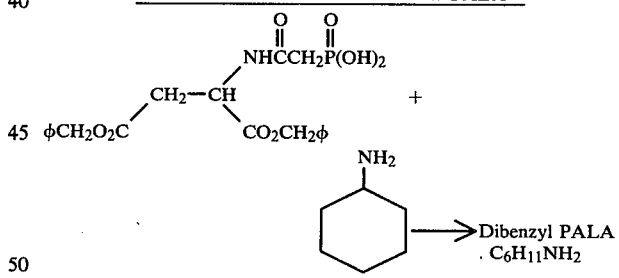

→ Dibenzyl PALA · $C_6H_{11}NH_2$

To prevent the formation of these impurities would require more extensive research and possible routing alterations. The decision was made to minimize their formation, then remove the phosphorus contamination from the dibenzyl PALA. This was carried out by the method as shown in schematic in FIG. VI.

Upon preparation of the cyclohexylammonium salt of dibenzyl PALA, the dibenzyl PALA liberated from this purified salt was analyzed and found to give 1 peak in the $P^{31}$NMR. In addition, both the liberated dibenzyl PALA and the amine salt were subjected to the hydrolysis and partial neutralization steps. The $P^{31}$ spectra of the resultant disodium PALA samples confirmed that the phosphorus impurities could be eliminated by this salt formation.

In addition to eliminating the phosphorus contaminants, the amine salt formation also removes the unreacted dibenzyl aspartate. This results in a final product free of aspartic acid contamination.

Scale-up development for the preparation of the pure salt has overcome some potentially serious manipulative problems. The salt is prepared by adding from about 0.9 to about 1.0 equivalent of cyclohexylamine to an acetone solution of dibenzyl PALA. The product is insoluble in acetone whereas a large percentage of the impurities remain in solution. It was found that the reaction must be run under anhydrous conditions with gentle mixing of the reactants, otherwise a gelatinous product will result. On a multi-kilogram scale, this material would be nearly impossible to isolate. The purity of the product is upgraded to an acceptable level by recrystallization from absolute methanol.

Difficulties are encountered in the use of dioxane for the preparation of dibenzyl PALA. As mentioned, triethylamine hydrochloride is an insoluble by-product of the reaction, and large volumes of solvent are required in order to maintain sufficient stirring. In addition, the reaction is exothermic, and the use of dioxane limits the extent of cooling to ~12°, which is the temperature at which dioxane freezes.

The solvent substituted for dioxane in this reaction was methylene chloride. This solvent offers the following advantages: (a) It is nonflammable; (b) It allows for a lower cooling temperature; (c) The volume of solvent is reduced in half; (d) The removal of triethylamine hydrochloride by filtration is eliminated since it is soluble in the reaction mixture; and (e) The evaporation of the solvent prior to work-up is no longer necessary.

The work-up involves aqueous washes of the methylene chloride solution in order to remove unreacted acid chloride and triethylamine hydrochloride. A considerable emulsion problem was encountered during this washing procedure. This difficulty has been eliminated by substituting diluted hydrochloric acid for the water.

Additional process improvements include the fact that the cyclohexylammonium salt is hydrolyzed directly to the tetrasodium PALA. This eliminates the extra manipulation of releasing the dibenzyl PALA from the amine salt prior to hydrolysis.

Another improvement is the azeotropic removal of water from the hygroscopic dibenzyl PALA with chloroform prior to salt formation. This results in a more crystalline salt and ultimately in a higher yield.

A final point is that the volume of water required for the hydrolysis has been reduced by 63% over that used in the initial synthetic work. This, of course, allows for larger scale runs to be made using the same size equipment. At the bench scale, using as a maximum 50 l. flasks, this procedure has been used to prepare disodium PALA in ~2 kg. lots. Incorporating all of the described modifications, a run using 50 and 100 gallon Pfaudlers has been successfully carried out. At full scale, ~15 kg. of the target material can be produced per run using this size equipment. The process, as currently developed, is limited only by the size of the equipment.

By the present method, the purity of the desired material has been upgraded to a satisfactory IND level. This was accomplished by (1) completely eliminating acetic acid and sodium acetate through a turbulent flow precipitation; (2) a convenient washing procedure which eliminates the acetic acid and sodium acetate and reduces the ethanol content; and (3) by preparing the cyclohexylammonium salt of dibenzyl PALA which removes the aspartic acid and phosphorus-containing contaminants. In addition, the procedure has been optimized for ease of scale-up, and the problems of process manipulations have been solved.

Example 9 provides one sequence of steps in preparing the disodium salt of PALA while Example 10 provides a separate sequence of steps for the preparation of the disodium salt of PALA.

EXAMPLE 9

Phosphonoacetyl chloride (III)

A 50-gallon Pfaudler reactor was purged with nitrogen to a measured oxygen content of <3%, then charged with methylene chloride (21 l.), 1, 2-dimethoxyethane (16 l.), N,N-dimethylformamide (1.76 l.), and phosphonoacetic acid (II) (16.0 kg.; 114 moles). The stirred mixture was cooled to 5°, then thionyl chloride (28.56 kg.; 240.0 moles) was added in a thin stream during 3 hours. The temperature of the reaction mixture was maintained between 10° and 15° during the addition. The resulting solution was heated at 30° for 3 hours, then the temperature was increased to 43° during the next hour. Additional methylene chloride (20.0 l.) was added, then the stirred solution was cooled (0°) and stored for 12 hours at 0°–3°. To this solution was added water (2.44 l.; 137 moles), dissolved in 1,2-dimethoxyethane (8.0 l.), in a thin stream over a period of 4 hours while maintaining the reaction temperature between 0° and 3°. After the addition was completed, the solution was stirred an additional 0.5 hour at 0°, then immediately used in the next reaction.

L-Aspartic acid, N-(phosphonoacetyl)-, dibenzyl ester (IV)

A 100-gallon Pfaudler reactor purged with nitrogen was charged in succession with methylene chloride (120 l.), L-aspartic acid, dibenzyl ester p-toluenesulfonate (40.75 kg.; 83.93 moles), and triethylamine (58.6 l.). The stirred solution was cooled to 5°, then the phosphonoacetyl chloride (III) (114.3 moles) was added in a thin stream during 3 hours while the temperature was maintained between 10° and 18°. Additional triethylamine (6.0 l.) was added, and the mixture was stirred an additional 0.5 hour, then stored for 12 hours at room temperature. Methylene chloride (120 l.) was added, and the solution was washed in succession with 10% aqueous hydrochloric acid (2×114 l.), 5aqueous hydrochloric acid (3×114 l.), and water (114 l.). The organic layer was dried over sodium sulfate (34.2 kg.) and magnesium sulfate (6.9 kg.) then concentrated in vacuo to 75 l. in a 100-gallon Pfaudler. Trace amounts of water were removed by co-distillation with chloroform (150 l. and 190 l.). Trace amounts of chloroform were removed by co-distillation with acetone (150 l.). The resulting thick oil was diluted with acetone (300 l.), then used immediately in the next reaction.

L-Aspartic acid, N-(phosphonoacetyl)-, dibenzyl ester, complexed with cyclohexylamine Cyclohexylamine (7478 g.; 75.54 moles) was added, in a thin stream, to a gently stirred solution of L-aspartic acid, N-(phosphonoacetyl)-, dibenzyl ester (IV) (36.50 kg.; 83.93 moles) in acetone (300 l.) at 20° during 20 minutes. The resulting mixture was stored for 12 hours at 5°–10°, then the precipitate was collected and washed with acetone (70 l.). The material was resuspended in acetone (230 l.), stirred for 30 minutes, collected, washed with additional acetone (2×30 l.), then dried in vacuo (40°) to give 33.45 kg. (74.7%) of product. This material (33.2 kg.) was suspended in boiling methanol (527 l.). Celite (1.7 kg.) and cellulose (500 g.) were added, and the suspension was heated at reflux for 3 hours. Insolubles were removed by filtration (Celite). The clear filtrate was diluted with acetone (400 l.), and the resulting mixture was stored for 16 hours at 5°–10°. The precipitated solid was collected, washed with acetone (40 l.), then dried in vacuo (40°) to give 17.49 kg. (52.6% recovery) of purified product. The mother liquor was concentrated in vacuo, and an additional 7.31 kg. of material was obtained to give a total of 24.80 kg. (75% recovery) of purified product.

L-Aspartic acid, N-(phosphonoacetyl)-, tetrasodium salt (V)

To a cold (2°), stirred solution of sodium hydroxide (97%) (7.532 kg,; 182.7 moles) in distilled water (114 l.) was added L-aspartic acid, N-(phosphonoacetyl)-, dibenzyl ester, complexed with cyclohexylamine (23.8 kg.; 44.5 moles) during 30 minutes while maintaining the temperature of the mixture at 10°–15°. The mixture was stirred at 15° for 4 hours then stored at 10° for 16 hours. The aqueous solution was washed with methylene chloride (4×75 l.). Decolorizing carbon (700 g.) and Celite (1 kg.) were added to the aqueous solution. The mixture was stirred for 30 minutes then clarified by filtration. The filtrate was diluted with ethanol (410 l.) then stored at 10° for 8 hours. The supernatant alcohol layer was removed, and the heavy oil washed with additional ethanol (6.5 l.) then immediately used in the next reaction.

L-Aspartic acid, N-(phosphonoacetyl)-, disodium salt.1.3 H$_2$O.0.13 EtOH

Glacial acetic acid (70.0 l.) was added to the L-aspartic acid, N-(phosphonoacetyl)-, tetrasodium salt oil from the above reaction. The mixture was stirred at room temperature for 30 minutes, clarified by filtration, then ethanol (238 l.) was added to the stirred solution during 1.75 hours. The mixture was stirred an additional hour then stored at 10° for 20 hours. The resulting precipitate was collected then washed with ethanol (12.0 l.). This material was washed by resuspension with 92% ethanol—8% water (60 gal.) at 27° for 15 hours in a 100-gallon Pfaudler reactor. The solid was collected then washed on the filter with absolute ethanol (4×1.5 gal.). The solid was washed a second time with 92% ethanol—8% water (60 gal.) at 26° for 15 hours. The solid was collected, washed on the filter with absolute ethanol (5×2 gal.), then dried to constant weight in vacuo (first at room temperature, then at 40°) to give 12,154 g. (76%) of purified product. The melting point of this material is non-determinant.

Anal.

Calc'd. for C$_6$H$_{7.7}$NO$_8$P . 2.3 Na . 1.3 H$_2$O . 0.13 EtOH

|  | C | H | N | P | Na |
|---|---|---|---|---|---|
|  | 22.44 | 3.33 | 4.18 | 9.24 | 15.78 |
| Found | 22.69 | 3.43 | 4.20 | 9.27 | 15.81 |

Sodium analysis indicates a composition of
70% di-NaPALA
30% tri-NaPALA
Based on empirical formula and spectral data,
% H$_2$O=7.0%
% EtOH=1.8%

Spectral Data:

Infrared (Nujol)

Major bands: 3400-3200, 2920, 2850, 1730-1690, 1650-1580, 1460, 1370, 1170-1140, 1070-1030, 910-870 cm$^{-1}$ Nuclear Magnetic Resonance (D$_2$O)

δ 4.70 (HOD); 4.50 (t, 1, —CH—, J=6.0 Hz); 3.60 (q, 0.3, —CH$_2$— of ethanol, J=7.0 Hz); 3.00-2.50 (m, 4, methylene H); 1.15 (t, 0.4, —CH$_3$ of ethanol, J=7.0 Hz)

| Optical Rotation: | |
|---|---|
| Observed | Literature |
| $[\alpha]_D^{23}$ + 14.56° (c, 0.206 in H$_2$O) | $[\alpha]_D^{22}$ + 14.86° (c, 1.998 in H$_2$O) |

Chromatography:

Thin Layer Chromatography
(Cellulose Quanta/Gram Q2F Glass Plates)

| Solvent System | R$_f$ Value |
|---|---|
| 1. Lithium chloride (0.6 M)-ethanol-ammonium hydroxide (5:5:1) | 0.47 |
| 2. Ethanol-water (2:3) | 0.78 |
| 3. water (6:1:3) (elongated) | 0.22 |
| 4. n-Butanol-acetic acid-water (5:2:3) | 0.30 (Tailing) |

Detection: (a) Ninhydrin (b) Phospray
Quantity Spotted: 300 μg.
Results: The compound moves as one phospray positive spot in each of the solvent systems. No aspartic acid was observed on spraying with ninhydrin.

EXAMPLE 10

Phosphonoacetyl chloride (III)

To a stirred mixture of phosphonoacetic acid (II) (2000 g.; 14.28 moles), N, N-dimethylformamide (208.8 g.; 2.856 moles), and dioxane (7.15 l.) was added, dropwise, thionyl chloride (3568 g.; 29.99 moles) during 1.5 hours. The temperature was maintained below 30° during the addition. The resulting solution was heated at 45° for 2.5 hours then cooled to 5°. Water (283 ml.; 15.7 moles) dissolved in dioxane (2.5 l.) was then added, dropwise, over a period of 2 hours. The temperature was kept below 10° during the addition. This solution of acid chloride (III) was stirred at 5°–10° for 40 minutes then used in the following reaction without further characterization. A second chlorination was carried out concurrently, under the same conditions, using identical quantities of reactants.

L-Aspartic acid, N-(phosphonoacetyl)-, dibenzyl ester (IV)

A stirred suspension of L-aspartic acid, dibenzyl ester p-toluenesulfonate (I) (4625 g.; 9.525 moles) in dioxane (20.0 l.) was cooled to 15°, then triethylamine (4820 g.; 47.63 moles) was added, in a thin stream, during 1 hour. The resulting solution was stirred for 20 minutes, then the above solution of phosphonoacetyl chloride (III), prepared from 14.28 moles of the corresponding acid, was added, dropwise, over a period of 5 hours. The temperature was maintained below 20° during the addition. Additional triethylamine (1162 g.; 11.48 moles) was added and the reaction mixture was stirred for 1 hour. After standing for 8 hours at room temperature, the mixture was diluted with acetone (5.5 l.), stirred for 15 minutes, then the insolubles were collected on a filter and washed with dioxane (10.0 l.). A second reaction was carried out concurrently, under the same conditions, using identical amounts of materials. The filtrates from the two runs were combined and spin-evaporated in vacuo. The residue (orange, viscous oil) was dissolved in methylene chloride (110.0 l.), then the organic solution was gently washed with water (6×30.0 l.). After drying the solution over sodium sulfate (11.3 kg.) and magnesium sulfate (2.3 kg.), the insolubles were filtered off (Celite pad), and the filtrate was evaporated in vacuo to constant weight; yield of dibenzyl PALA (IV) 7970 g. (96.1%). This yellow, viscous oil was suitable for further transformation.

L-Aspartic acid, N-(phosphonoacetyl)-, dibenzyl ester, complexed with cyclohexylamine Cyclohexylamine (1815 g.; 18.30 moles) was added, dropwise, to a cold (7°), stirred solution of L-aspartic acid, N-(phosphonoacetyl)-, dibenzyl ester (IV) (7970 g.; 18.30 moles) in acetone (24.0 l.) during 1.25 hours. The temperature was maintained below 15° during the addition. The cooling bath was removed, and the resulting mixture was stirred for 1 hour. The mixture was stored at room temperature for 6 hours, then the precipitated solid was collected on a filter, washed with acetone (15.0 l), and dried; yield, 4932 g.; m.p., 176.5°–177.5°. This material was recrystallized from boiling methanol (35.0 l.) then dried to give 1663 g. of the purified salt; m.p., 178°–181°; literature m.p., 186°–188°. The mother liquor was concentrated in vacuo to a volume of 20.0 l. The solution was diluted with acetone (16.0 l.) and cooled (−10°) to give an additional 967 g. of product; m.p., 177°–180°. A third crop of material (429 g.) was obtained by evaporating the above methanol-acetone filtrate to near dryness and suspending the residue in acetone (5.0 l.); total amount of the purified amine salt suitable for further transformation, 3059 g. (62.0% recovery).

L-Aspartic acid, N-(phosphonoacetyl)-, tetrasodium salt (V)

To a cold (5°), stirred solution of sodium hydroxide (1291 g.; 32.28 moles) in water (20.5 l.) was added, in portions, during 30 minutes, L-aspartic acid, N-(phosphonoacetyl)-, dibenzyl ester, complexed with cyclohexylamine (3059 g.; 5.378 moles if the amine salt has the same empirical formula as the analytically pure sample). The reaction mixture was stirred at 5°–15° for 3.5 hours, then extracted with methylene chloride (2×8.5 l.) and ether (1×8.5 l.). The aqueous solution was clarified by filtration, concentrated in vacuo (<35°; 3–5 mm. Hg) to a volume of 14.6 l., then diluted with ethanol (51.4 l.). The resulting mixture was stirred for 1 hour and stored at room temperature for 12 hours. The aqueous ethanol solution was removed giving crude (V) as a light yellow oil suitable for further transformation.

L-Aspartic acid, N-(phosphonoacetyl)-, disodium salt

Glacial acetic acid (8.0 l.) was added to the above precipitated oil [crude L-aspartic acid, N-(phosphonoacetyl)-, tetrasodium salt (V) prepared from 3059 g. of the amine salt]. The mixture was stirred at room temperature for 30 minutes, then a gelatinous insoluble was filtered off. The clear, light yellow filtrate was diluted with ethanol (24.0 l.). The resulting mixture was stirred for 1.75 hours, then the precipitated material was collected on a filter. The solid was suspended in ethanol (14.5 l.), and the mixture was vigorously stirred for 1 hour. The product was collected on four filters then partially dried by spin-evaporation in vacuo (30°–45°; aspirator pressure then 3–5 mm. Hg). The lumpy material (2870 g.) was dissolved in water (5.25 l.), the solution was clarified by filtration, then the filtrate (~6.9 l. volume) was diluted with ethanol (21.0 l.). The resulting mixture was stirred for 30 minutes, then the precipitated oil was allowed to settle (1 hour). The aqueous ethanol solution was removed, and the oil was washed once with ethanol (4.3 l.). This material was dissolved in water (8.15 l), and the solution (9.8 l.) was divided into three portions (two of 4.0 l.; one of 1.8 l.). Each portion was added, during 13 hours, to the vortex of vigorously stirred ethanol (10×aqueous volume: 2×40.0 l.; 1×18.0 l.). After stirring the mixtures for 2 hours, the water-ethanol solutions were siphoned off, and the solid from the three precipitations was combined. The material was stirred for 30 minutes in ethanol (10.0 l.), collected on a filter, then dried to constant weight in vacuo at room temperature over phosphorus pentoxide. The dried product (1748.0 g.) was passed through a 150μ, stainless steel sieve and thoroughly blended to give the disodium PALA as a white powder.

| Anal. | | | | | |
|---|---|---|---|---|---|
| Calc'd. for $C_6H_{7.6}NO_8P \cdot 2.4\ Na \cdot 2\ H_2O \cdot 0.5\ C_2H_6O$ | | | | | |
| | C | H | N | P | Na |
| | 22.91 | 4.01 | 3.82 | 8.44 | 15.04 |
| Found | 23.16 | 3.76 | 3.79 | 8.57 | 15.18 |

Sodium analysis indicates a composition of
60% di-Na PALA
40% tri-Na PALA
Based on the empirical formula,
% $H_2O$ = 9.8%
% EtOH = 6.3%

Spectral Data:

Nuclear Magnetic Resonance ($D_2O$)

$\delta$ 1.17 (t, 1.5, —$CH_3$ of ethanol); 2.74 (d, 2, —$CH_2$ α to —CH); 2.77 (d, 2, J=20 Hz, —$CH_2$ α to P); 3.63 (q, 1, —$CH_2$ of ethanol); 4.48 (t, 1, —CH)

| Optical Rotation: | |
|---|---|
| Observed | Literature |
| $[\alpha]_D^{22.5}$ + 14.73 (c, 2.098 in water) | $[\alpha]_D^{22}$ + 14.86 (c, 1.998 in water) |

| Thin Layer Chromatography (Cellulose, Quanta/Gram Q2F Glass Plates) | |
|---|---|
| Solvent System | $R_f$ Value |
| 1. Lithium chloride (0.6 M)-ethanol-ammonium hydroxide | |
| 2. Ethanol-water (2:3) | 0.72 |
| 3. Ethanol-ammonium hydroxide- | (elongated) |
| 4. n Butaol-acetic acid-water (5:2:3) | 0.22 (tailing) |

Detection: (a) Ninhydrin (b) Phospray

Results: The compound moves as one phospray positive spot in each of the solvent systems. No aspartic acid was observed on spraying with ninhydrin.

It is through that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. In a method for the preparation of a sodium salt of N-(phosphonoacetyl)-L-aspartic acid, the improvement which comprises reacting L-aspartic acid with benzyl alcohol and p-toluenesulfonic acid monohydrate to obtain L-aspartic acid, dibenzyl ester p-toluenesulfonate, and reacting said L-aspartic acid, dibenzyl ester p-toluenesulfonate with triethylamine, followed by the addition of phosphonoacetyl chloride to produce the N-(phosphonoacetyl)-L-aspartic acid moiety in the form of the dibenzyl ester, wherein the carboxyl groups of the N-(phosphonoacetyl)-L-aspartic acid are esterified and unreacted phosphonoacetyl chloride is separated therefrom, and hydrolyzing the dibenzyl ester to obtain a sodium salt of N-(phosphonoacetyl)-L-aspartic acid.

2. The method of claim 1, wherein separation of the dibenzyl ester of N-(phosphonoacetyl)-L-aspartic acid and unreacted phosphonoacetyl chloride is accomplished by washing with water, and including the step of subjecting said dibenzyl ester to hydrolysis to obtain a product mixture containing the tetrasodium salt.

3. The method of claim 2, further including the steps of subjecting the product mixture to an ion exchange procedure to obtain N-(phosphonoacetyl)-L-aspartic acid in the free acid form, titrating said free acid to a pH of 9.2 and recovering the purified tetrasodium salt.

4. The method of claim 2, further including the step of dissolving said product mixture in glacial acetic acid, diluting the resulting solution with ethanol to precipitate the disodium salt and recovering said disodium salt.

5. The method of claim 1, further including the steps of reacting the lastformed dibenzyl ester with N,N'-dibenzylethylenediamine to produce the N,N'-dibenzylethylenediamine salt of the dibenzyl ester, and including subjecting said salt to hydrolysis to produce a product mixture containing the tetrasodium salt, dissolving said product mixture in glacial acetic acid, diluting the resulting solution with ethanol to precipitate the disodium salt and recovering said disodium salt.

6. The method of claim 1, wherein perchloroethylene is employed as the esterification medium in the reaction of L-aspartic acid with benzyl alcohol and p-toluenesulfonic acid monohydrate.

7. In a method for the preparation of a sodium salt of N-(phosphonoacetyl)-L-aspartic acid by reacting L-aspartic acid, dibenzyl ester p-toluenesulfonate with triethylamine, followed by the addition of phosphonoacetyl chloride to produce the N-(phosphonoacetyl)-L-aspartic acid moiety in the form of the dibenzyl ester, wherein the carboxyl groups of the N-(phosphonoacetyl)-L-aspartic acid are esterified, adding cyclohexylamine under anhydrous conditions to produce the cyclohexylamine salt of said dibenzyl ester, reacting said cyclohexylamine salt with sodium hydroxide to produce L-aspartic acid, N-(phosphonoacetyl)-, tetrasodium salt, and reacting said tetrasodium salt with acetic acid to produce L-aspartic acid, N-(phosphonoacetyl)-, disodium salt, the improvement which comprises precipitating the obtained disodium salt twice from water using ethanol, the second precipitation including a dropwise addition of an aqueous solution of said disodium salt to a vortex of vigorously stirred ethanol, thereby removing impurities in the form of acetic acid and sodium acetate.

* * * * *